US011207218B2

(12) United States Patent
Kato et al.

(10) Patent No.: US 11,207,218 B2
(45) **Date of Patent: *Dec. 28, 2021**

(54) METHOD FOR PRODUCING ABSORBER AND METHOD FOR PRODUCING ABSORBENT ARTICLE

(71) Applicant: Kao Corporation, Tokyo (JP)

(72) Inventors: Yuki Kato, Utsunomiya (JP); Ryuji Matsunaga, Utsunomiya (JP); Takuaki Harada, Kaminokawa-machi (JP); Tomoyuki Motegi, Kaminokawa-machi (JP); Hiroyuki Iwasa, Tachikawa (JP)

(73) Assignee: KAO CORPORATION, Tokyo (JP)

( * ) Notice: Subject to any disclaimer, the term of this patent is extended or adjusted under 35 U.S.C. 154(b) by 144 days.

This patent is subject to a terminal disclaimer.

(21) Appl. No.: 16/608,660

(22) PCT Filed: Nov. 28, 2017

(86) PCT No.: PCT/JP2017/042688

§ 371 (c)(1),
(2) Date: Oct. 25, 2019

(87) PCT Pub. No.: WO2019/106731

PCT Pub. Date: Jun. 6, 2019

(65) Prior Publication Data

US 2020/0138637 A1 May 7, 2020

(51) Int. Cl.
*A61F 13/15* (2006.01)
*B29L 31/48* (2006.01)

(52) U.S. Cl.
CPC .. *A61F 13/15764* (2013.01); *A61F 13/15634* (2013.01); *A61F 13/15674* (2013.01);
(Continued)

(58) Field of Classification Search
None
See application file for complete search history.

(56) References Cited

U.S. PATENT DOCUMENTS

| | | | | |
|---|---|---|---|---|
| 4,666,647 | A | 5/1987 | Enloe et al. | |
| 2002/0147434 | A1* | 10/2002 | Mori | A61F 13/531 604/365 |

(Continued)

FOREIGN PATENT DOCUMENTS

| | | | |
|---|---|---|---|
| CN | 101647741 | A | 2/2010 |
| CN | 102665630 | A | 9/2012 |

(Continued)

OTHER PUBLICATIONS

Machine translation of WO 2017/038963 (Year: 2017).*
International Search Report, issued in PCT/JP2017/042688, dated Feb. 20, 2018.

*Primary Examiner* — Barbara J Musser
(74) *Attorney, Agent, or Firm* — Birch, Stewart, Kolasch & Birch, LLP

(57) ABSTRACT

An absorbent member manufacturing method of the present invention is a method for manufacturing an absorbent member (100) for an absorbent article and including synthetic fibers (10*b*) and hydrophilic fibers (10*a*). The method involves: a transporting step of transporting the hydrophilic fibers (10*a*) and a plurality of sheet fragments (10*bh*) to an accumulating depression (41) by using a duct (3); an accumulating step of accumulating, in the accumulating depression (41), the plurality of sheet fragments (10*bh*) and the hydrophilic fibers (10*a*), and obtaining an accumulation (100*a*) which is a constituent member of the absorbent member (100); and a depression forming step of forming a depression (100*e*) in the accumulation (100*a*) by applying pressure to a portion thereof. In the transporting step, the sheet fragments (10*bh*) and the hydrophilic fibers (10*a*) are brought into contact with one another in an airflow created inside the duct (3), and the sheet fragments (10*bh*) and the hydrophilic fibers (10*a*) are transported by the airflow in a
(Continued)

dispersed and airborne state in which the sheet fragments and the hydrophilic fibers are mixed.

18 Claims, 5 Drawing Sheets

(52) U.S. Cl.
CPC .................... *A61F 13/15723* (2013.01); *A61F 2013/15715* (2013.01); *B29L 2031/4878* (2013.01)

(56) References Cited

U.S. PATENT DOCUMENTS

| | | | | |
|---|---|---|---|---|
| 2006/0009743 | A1 | 1/2006 | Wang et al. | |
| 2010/0174259 | A1 | 7/2010 | Mori | |
| 2012/0280434 | A1 | 11/2012 | Hoshika et al. | |
| 2014/0308483 | A1* | 10/2014 | Li | A61F 13/536 428/167 |
| 2019/0201247 | A1* | 7/2019 | Tsukuda | A61F 13/15642 |

FOREIGN PATENT DOCUMENTS

| | | | | |
|---|---|---|---|---|
| CN | 103057853 | A | 7/2014 | |
| EP | 0 608 884 | A1 | 8/1994 | |
| JP | 2002-301105 | A | 10/2002 | |
| JP | 2006-345980 | A | 12/2006 | |
| JP | 2010-142299 | A | 7/2010 | |
| JP | 2015-112393 | A | 6/2014 | |
| JP | 2015-112393 | A | 6/2015 | |
| JP | 2017-47212 | A | 3/2017 | |
| JP | 2019-63367 | A | 4/2019 | |
| JP | 2019-63368 | A | 4/2019 | |
| JP | 2019-63369 | A | 4/2019 | |
| JP | 2019-63370 | A | 4/2019 | |
| JP | 2019-63371 | A | 4/2019 | |
| JP | 2019-63372 | A | 4/2019 | |
| JP | 2019-63374 | A | 4/2019 | |
| JP | 2019-63375 | A | 4/2019 | |
| JP | 2019-97613 | A | 6/2019 | |
| JP | 2019-97614 | A | 6/2019 | |
| JP | 2019-170952 | A | 10/2019 | |
| RU | 2 381 020 | C2 | 2/2010 | |
| WO | WO-2017038963 | A1 * | 3/2017 | A61F 13/15 |
| WO | WO 2019/059385 | A | 4/2019 | |
| WO | WO 2019/069383 | A | 4/2019 | |
| WO | WO 2019/069384 | A | 4/2019 | |

* cited by examiner

METHOD FOR PRODUCING ABSORBER AND METHOD FOR PRODUCING ABSORBENT ARTICLE

TECHNICAL FIELD

The present invention relates to a method for manufacturing an absorbent member for an absorbent article, and a method for manufacturing an absorbent article.

BACKGROUND ART

A known example of an absorbent member used in an absorbent article, such as a disposable diaper, a sanitary napkin or an incontinence pad, is an absorbent member including pulp fibers and synthetic fibers. The inclusion of synthetic fibers in the absorbent member can impart softness to the absorbent member and can also allow body fluid to be absorbed quickly. Patent Literature 1 is a known example describing a method for manufacturing an absorbent member including pulp fibers and synthetic fibers.

Patent Literature 1 describes a method for manufacturing an absorbent member for an absorbent article, the method involving: shaping a nonwoven fabric having a three-dimensional structure in which fibers have been bound together in advance; then forming nonwoven fabric fragments by pulverizing the nonwoven fabric; and mixing the nonwoven fabric fragments with hydrophilic fibers. Patent Literature 1 describes employing a cutter mill system as a means for pulverizing the nonwoven fabric.

CITATION LIST

Patent Literature

Patent Literature 1: JP 2002-301105A

SUMMARY OF INVENTION

The present invention is a method for manufacturing an absorbent member for an absorbent article and including synthetic fibers and hydrophilic fibers. The manufacturing method involves: a transporting step of transporting the hydrophilic fibers and a plurality of sheet fragments including the synthetic fibers to an accumulating portion by using a transporting portion; an accumulating step of accumulating, in the accumulating portion, the plurality of sheet fragments and the hydrophilic fibers transported in the transporting step, and obtaining an accumulation which is a constituent member of the absorbent member; and a depression forming step of forming a depression in the accumulation obtained in the accumulating step by applying pressure to a portion of the accumulation. In the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed.

Further, the present invention is a method for manufacturing an absorbent article that includes a liquid-permeable topsheet forming a skin-facing surface, a backsheet forming a non-skin-facing surface, and an absorbent member interposed between the topsheet and the backsheet. The manufacturing method involves: a transporting step of transporting hydrophilic fibers and a plurality of sheet fragments including synthetic fibers to an accumulating portion by using a transporting portion; an accumulating step of accumulating, in the accumulating portion, the plurality of sheet fragments and the hydrophilic fibers transported in the transporting step, and obtaining an accumulation which is a constituent member of the absorbent member; a topsheet superposing step of superposing the topsheet on an upper surface side of the accumulation; a backsheet superposing step of superposing the backsheet on a lower surface side of the accumulation; and a depression forming step of forming a depression in the accumulation by applying pressure to a portion of the accumulation. In the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed.

DESCRIPTION OF EMBODIMENTS

When nonwoven fabric fragments are formed by pulverizing a nonwoven fabric by using a cutter mill system as in the absorbent member manufacturing method disclosed in Patent Literature 1, it is difficult to form nonwoven fabric fragments that all have a predetermined size, and there are variations with respect to the intended size. Further, the formed nonwoven fabric fragments are likely to become fuzzy, which may cause the nonwoven fabric fragments to get connected to one another and form an absorbent member in a state where the fragments are not dispersed, thereby creating unevenness in the structure of the absorbent member. If depressions are to be formed in such an absorbent member by applying pressure to portions thereof, there may be sections that are difficult to crush by applying pressure or sections in which formability of depressions is poor. Patent Literature 1 neither discloses nor suggests a method for suppressing such deterioration in formability of depressions.

In view of the aforementioned circumstances, the present invention provides, for a method for manufacturing an absorbent member that includes hydrophilic fibers and sheet fragments including synthetic fibers, an absorbent member manufacturing method in which deterioration in formability of depressions is suppressed. The present invention also provides, for a method for manufacturing an absorbent article including an absorbent member that includes hydrophilic fibers and sheet fragments including synthetic fibers, an absorbent article manufacturing method in which deterioration in formability of depressions is suppressed.

The present invention is described below according to preferred embodiments thereof with reference to the drawings.

The manufacturing method of the present invention is a method for manufacturing an absorbent member including synthetic fibers and hydrophilic fibers, and for manufacturing an absorbent article including the absorbent member. The absorbent member manufactured according to the present invention is an absorbent member for an absorbent article. An absorbent article is used for absorbing and retaining body fluid excreted from the body, with examples mainly including urine and menstrual blood. Examples of absorbent articles include disposable diapers, sanitary napkins, incontinence pads, and pantiliners, but are not limited thereto, and widely encompass articles used for absorbing liquids discharged from the human body. Typically, an absorbent article includes a liquid-permeable topsheet, a liquid-impermeable or water-repellent backsheet, and a liquid-retentive absorbent member interposed between the two sheets. The absorbent member is the absorbent member formed by the absorbent member manufacturing method of the present invention.

Figure 1:
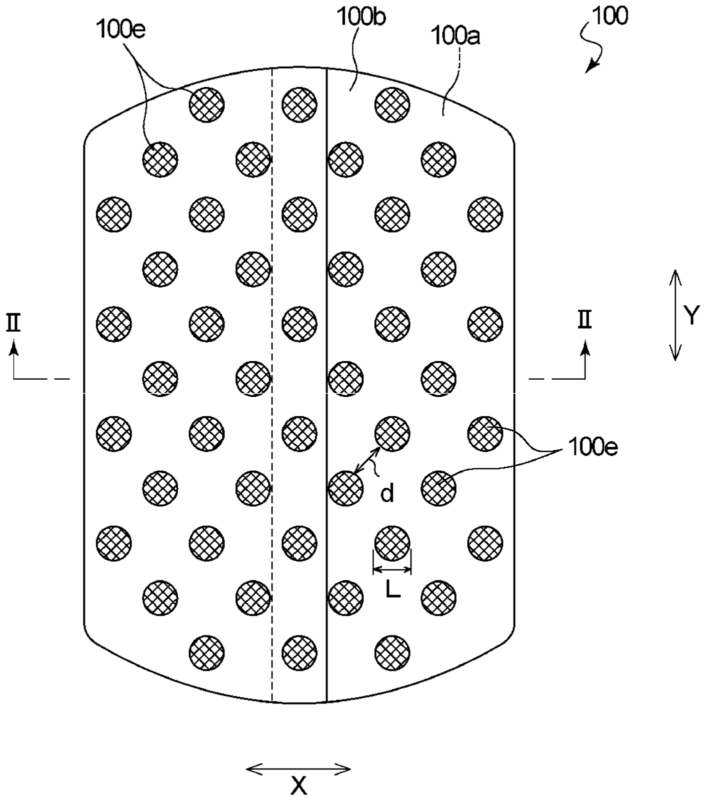
FIG. 1 is a plan view illustrating a preferred embodiment of an absorbent member manufactured by an absorbent member manufacturing method of the present invention.
Figure 2:
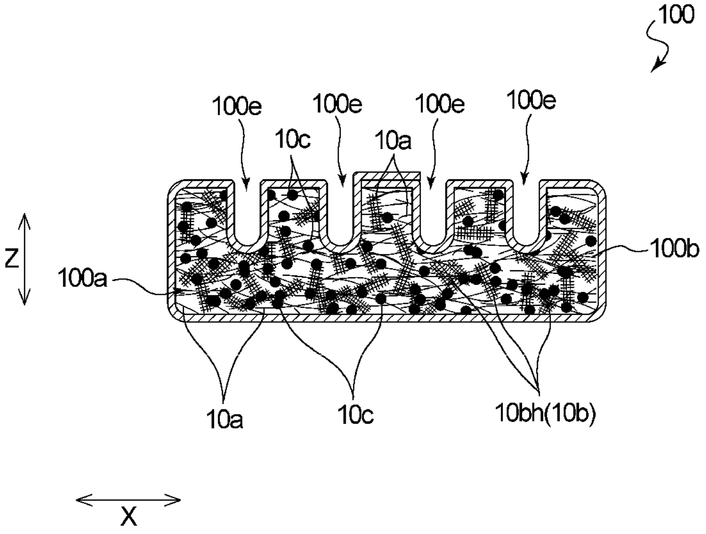
FIG. 2 is a cross-sectional view taken along line II-II of the absorbent member illustrated in FIG. 1.

FIG. 1 illustrates a plan view of an embodiment of an absorbent member 100 manufactured by the absorbent member manufacturing method of the present embodiment. FIG. 2 illustrates a cross-sectional view taken along line II-II of the absorbent member 100 illustrated in FIG. 1. The absorbent member 100 includes synthetic fibers 10*b* and hydrophilic fibers 10*a*. In the present embodiment, as illustrated in FIGS. 1 and 2, the absorbent member 100 includes an accumulation 100*a* including not only the synthetic fibers 10*b* and the hydrophilic fibers 10*a*, but also absorbent particles 10*c*. Herein, "include synthetic fibers 10*b*" refers to the inclusion of sheet fragments 10*bh* including the synthetic fibers 10*b*. The absorbent member 100 may suitably be a single layer or multi-layers including two or more layers so long as it includes the synthetic fibers 10*b* and the hydrophilic fibers. In the present embodiment, the absorbent member includes a single-layer accumulation 100*a* in which the hydrophilic fibers 10*a*, the synthetic fibers 10*b*, and the absorbent particles 10*c* are dispersed uniformly.

The accumulation 100*a* is a constituent member of the absorbent member 100, and the absorbent member 100 of the present embodiment is formed by covering the accumulation 100*a* with a core-wrap sheet 100*b*. The absorbent member 100 of the present embodiment has a shape that is long in the longitudinal direction, which corresponds to the front-rear direction of a wearer when the absorbent article is worn. Further, the absorbent member 100 of the present embodiment includes, in portions of the accumulation 100*a* covered by the core-wrap sheet 100*b*, a plurality of depressions 100*e* formed by applying pressure from above the core-wrap sheet 100*b*. As illustrated in FIG. 2, the depressions 100*e* are formed so as to be depressed in a recess form from the absorbent member 100's skin-facing surface side, which faces the wearer's skin when the absorbent article is worn, toward the non-skin-facing surface side. In the absorbent member 100, only the absorbent member 100's skin-facing surface side is depressed in a recess form. In the absorbent member 100, the depression 100*e* is formed of a compressed portion in which the density of constituent materials is relatively increased by compression. The depressions 100*e* in the absorbent member 100 can be formed by embossing the absorbent member 100 formed by wrapping the accumulation 100*a* with the core-wrap sheet 100*b*.

The shape of the depression 100*e*, in a planar view from the absorbent member 100's skin-facing surface side, may be any one of various shapes such as circular, elliptic, square, rectangular, or triangular. In the absorbent member 100, as illustrated in FIG. 1, the depression is circular. Further, as illustrated in FIG. 1, the depressions 100*e* are arranged in a substantially staggered arrangement. Herein "staggered arrangement" refers to an arrangement in which a plurality of rows of depressions 100*e*, each row including a plurality of depressions 100*e* arranged at even intervals in a first direction (Y direction), are arranged at even intervals in a second direction (X direction), and the depressions 100*e* closest to one another in the respective two rows of depressions 100*e* adjacent to one another in the second direction are shifted from one another by half a pitch.

It is preferable that the number of depressions 100*e* arranged per unit area is from 2 to 10 depressions/$cm^2$, more preferably from 5 to 8 depressions/$cm^2$. Further, the maximum diameter/length L in a planar view of the depression 100*e* is preferably 0.5 mm or greater, even more preferably 1 mm or greater, and preferably 8 mm or less, even more preferably 6 mm or less. In cases where the planar-view shape of the depression 100*e* is circular as illustrated in FIG. 1, the maximum diameter/length L is the diameter.

The accumulation 100*a* includes a plurality of sheet fragments 10*bh* including the synthetic fibers 10*b* (simply referred to hereinafter also as "sheet fragments 10*bh*"). Each sheet fragment 10*bh* has a substantially rectangular shape. The average length of the sheet fragments 10*bh* is preferably from 0.3 to 30 mm, more preferably from 1 to 15 mm, even more preferably from 2 to 10 mm. Herein, in cases where each sheet fragment 10*bh* is a rectangle, the average length refers to the average value of the length of a side in the longitudinal direction. In cases where each sheet fragment 10*bh* is a square, the average length refers to the average value of the length of any one of the four sides. When the average length of the sheet fragments 10*bh* is 0.3 mm or greater, a sparse structure can easily be formed in the absorbent member 100. When the average length is 30 mm or less, the absorbent member 100 is less likely to cause an unnatural feel to the wearer, and absorbency is less likely to become uneven depending on the positions within the absorbent member 100. The average width of the sheet fragments 10*bh* is preferably from 0.1 to 10 mm, more preferably from 0.3 to 6 mm, even more preferably from 0.5 to 5 mm. Herein, in cases where each sheet fragment 10*bh* is a rectangle, the average width refers to the average value of the length of a side in the lateral direction. In cases where each sheet fragment 10*bh* is a square, the average width refers to the average value of the length of any one of the four sides. When the average width of the sheet fragments 10*bh* is 0.1 mm or greater, a sparse structure can easily be formed in the absorbent member 100. When the average width is 10 mm or less, the absorbent member 100 is less likely to cause an unnatural feel to the wearer, and absorbency is less likely to become uneven depending on the positions within the absorbent member 100.

For the fiber materials forming the absorbent member 100, various materials conventionally used in absorbent members for absorbent articles can be used without particular limitation. Examples of the hydrophilic fibers 10*a* include pulp fibers, rayon fibers, and cotton fibers. Examples of the synthetic fibers 10*b* include short fibers made of polyethylene, polypropylene, or polyethylene terephthalate. The sheet fragments 10*bh* are not particularly limited so long as they are in a sheet form, but are preferably a nonwoven fabric. Examples of the absorbent particles 10*c* include starch-based, cellulose-based, synthetic polymer-based, and superabsorbent polymer-based particles. Examples of superabsorbent polymers that may be used include starch-acrylic acid (acrylate) graft copolymers, saponified products of starch-acrylonitrile copolymers, crosslinked products of sodium carboxymethyl cellulose, and acrylic acid (acrylate) polymers. For constituent members constituting the absorbent member 100, it is also possible to use, for example, deodorants and antibacterial agents as necessary. Examples of the core-wrap sheet 100*b* include tissue paper and liquid-permeable nonwoven fabrics.

Figure 3:
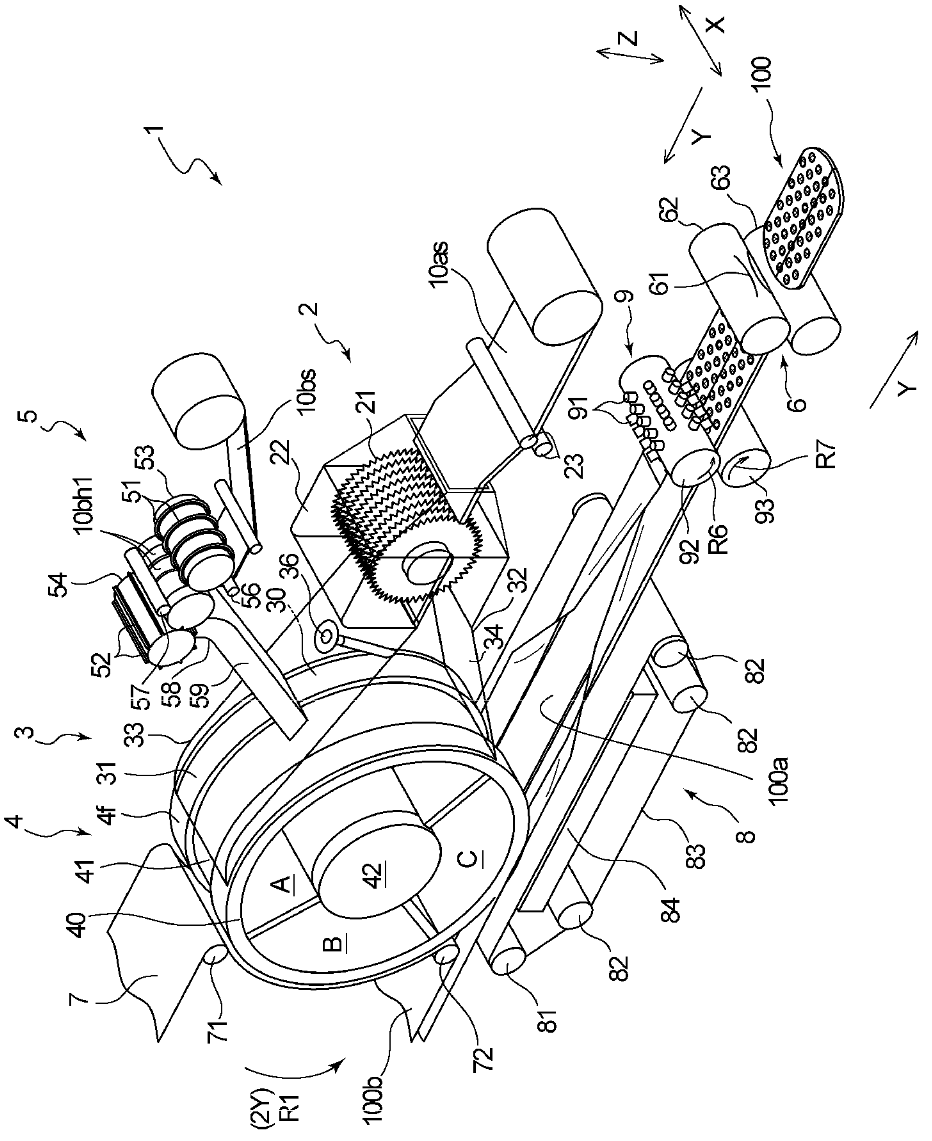
FIG. 3 is a schematic perspective view illustrating a preferred embodiment of a manufacturing device for manufacturing the absorbent member illustrated in FIG. 1.
Figure 4:
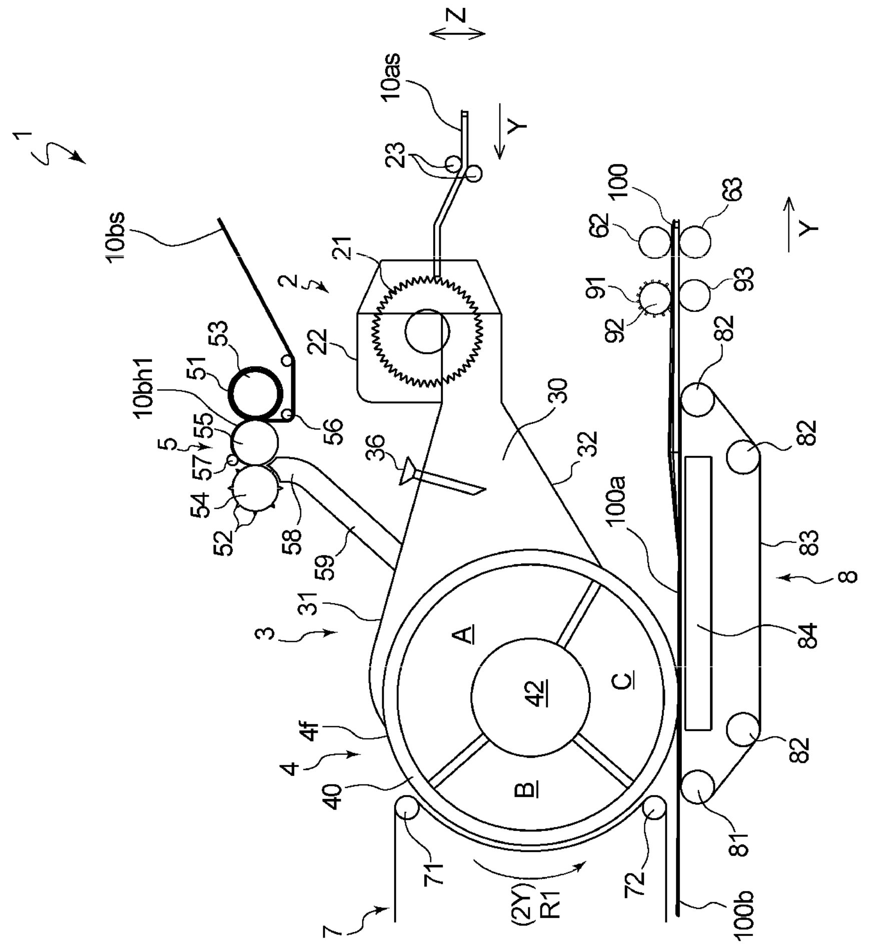
FIG. 4 is a schematic side view illustrating the manufacturing device illustrated in FIG. 3 as viewed from a lateral side.

Next, the absorbent member manufacturing method of the present invention is described with reference to FIGS. 3 to 9, taking, as an example, a method for manufacturing the absorbent member 100 according to the foregoing embodiment. FIGS. 3 and 4 illustrate an overall configuration of an embodiment of a manufacturing device 1 used for performing the manufacturing method of the present embodiment. On describing the method for manufacturing the absorbent member 100 of the present embodiment, first, the manufacturing device 1 of the present embodiment will be described.

The constituent members of the absorbent member 100 only need to include at least the synthetic fibers 10*b* and the hydrophilic fibers 10*a*, but the aforementioned absorbent member 100 includes the absorbent particles 10*c* in addition to the synthetic fibers 10*b* and the hydrophilic fibers 10*a*. As illustrated in FIGS. 3 and 4, the manufacturing device 1 for manufacturing the absorbent member 100 includes, from the upstream side toward the downstream side in the transporting direction: a defibrating portion 2 that defibrates a hydrophilic sheet 10*as* including the hydrophilic fibers 10*a* by using a defibrating machine 21; a duct 3, serving as a transporting portion, that transports the materials of the absorbent member 100 by carrying them on an airflow; a supplying portion 5 that supplies the sheet fragments 10*bh* to inside the duct 3 in midstream of the duct 3; a rotary drum 4 that is arranged downstream of the duct 3 adjacent thereto, and that includes an accumulating portion in which the materials of the absorbent member 100 are accumulated; a press-down belt 7 arranged along the rotary drum 4's outer circumferential surface 4*f* located on the opposite side from the duct 3; a vacuum conveyor 8 arranged below the rotary drum 4; a pressure application portion 9 arranged downstream of the vacuum conveyor 8: and a cutting device 6 arranged downstream of the pressure application portion 9. In the manufacturing device 1, an accumulating depression 41, serving as an example of the accumulating portion, is provided in the outer circumferential surface of the rotary drum 4.

In the description below, the direction in which the absorbent member 100 and a continuous synthetic fiber sheet 10*bs* including the synthetic fibers 10*b* are transported is the Y direction, the width direction of the synthetic fiber sheet 10*bs* and the absorbent member 100 being transported and the direction orthogonal to the transporting direction are the X direction, and the thickness direction of the synthetic fiber sheet 10*bs* and the absorbent member 100 being transported is the Z direction.

Further, the later-described first direction is the direction extending in the transporting direction Y, and refers to a direction wherein the angle formed between it and the transporting direction Y is within a range of less than 45 degrees. In the present embodiment, the first direction matches the direction parallel to the transporting direction Y.

Further, the later-described second direction is a direction intersecting with the first direction. In the present embodiment, the second direction is a direction orthogonal to the first direction, and matches the direction parallel to the width direction X of the synthetic fiber sheet 10*bs* and the absorbent member 100 being transported.

As illustrated in FIGS. 3 and 4, the manufacturing device 1 includes a defibrating portion 2 that defibrates a continuous hydrophilic sheet 10*as* including the hydrophilic fibers 10*a*. The defibrating portion 2 includes: a defibrating machine 21 that defibrates the hydrophilic sheet 10*as*; and a casing 22 that covers the upper side of the defibrating machine 21. The defibrating portion 2 is a section that supplies, to inside the duct 3, the defibrated hydrophilic fibers 10*a* which is a material of the absorbent member 100. In the manufacturing device 1, the defibrating portion 2 also includes a pair of feed rollers 23, 23 that supplies the hydrophilic sheet 10*as* to the defibrating machine 21.

Of the pair of feed rollers 23, 23, at least one roller is structured so as to be rotated by a driving device (not illustrated). The pair of feed rollers 23, 23 are nipping-type rollers. An example of the driving device is a servomotor. From the viewpoint of preventing slipping of the hydrophilic sheet 10*as*, it is preferable that both of the pair of feed rollers 23, 23 are rotated by the driving device. In this case, the pair of feed rollers 23, 23 may be driven directly by the driving device, or one of the rollers may be driven by the driving device and the drive may be transmitted to the other roller by a transmission means such as a gear. From the viewpoint of further preventing slipping of the hydrophilic sheet 10*as*, the pair of feed rollers 23, 23 may be made less slippery by forming, in the surface thereof, grooves extending in the axial direction over the entire circumference. In addition to the pair of feed rollers 23, 23, other rollers for assisting the transportation of the hydrophilic sheet 10*as* may be provided.

As illustrated in FIGS. 3 and 4, the manufacturing device 1 includes a duct 3, serving as the transporting portion, that transports the materials of the accumulation 100*a* of the absorbent member 100. The duct 3 extends from the defibrating portion 2 up to the rotary drum 4, and the duct 3's opening on the downstream side covers the outer circumferential surface 4*f* which is located at the rotary drum 4's space A which is maintained at a negative pressure. The duct 3 includes a top plate 31 forming the top surface, a bottom plate 32 forming the bottom surface, and side walls 33, 34 forming the respective side surfaces. By activating an air suction fan (not illustrated) of the rotary drum 4, an airflow for carrying the materials of the absorbent member 100 toward the outer circumferential surface 4*f* of the rotary drum 4 is created inside the space surrounded by the top plate 31, the bottom plate 32, and the side walls 33, 34 of the duct 3. Stated differently, the inside of the duct 3 serves as a flow path 30.

Further, as illustrated in FIGS. 3 and 4, the manufacturing device 1 has an absorbent particle dispersing tube 36 that supplies absorbent particles 10*c* into the duct 3, the absorbent particle dispersing tube being arranged at the top plate 31 of the duct 3. The absorbent particle dispersing tube 36 is configured such that the absorbent particles 10*c* are discharged, by a device such as a screw feeder (not illustrated), from a dispersing opening provided at the tip end of the absorbent particle dispersing tube 36, and are supplied into the flow path 30 of the duct 3. Further, the supply amount of the absorbent particles 10*c* to the absorbent particle dispersing tube 36 can be adjusted by the device such as a screw feeder (not illustrated).

As illustrated in FIGS. 3 and 4, the manufacturing device 1 includes a rotary drum 4. The rotary drum 4 has, in its outer circumferential surface 4*f*, an accumulating depression 41 which serves as an accumulating portion for accumulating the materials of the absorbent member to obtain an accumulation. The rotary drum 4 is cylindrical, and, by receiving motive power from a prime mover (not illustrated) such as a motor, a member 40 forming the outer circumferential surface 4*f* rotates in the direction of arrow R1 about a horizontal axis. The rotary drum 4 includes: a member 40 forming the outer circumferential surface 4*f*; and a drum body 42 located more inward than the member 40. The drum body 42 is fixed and does not rotate. In the manufacturing device 1, the accumulating depression 41 of the rotary drum 4 is arranged continuously over the entire circumference in the circumferential direction (2Y direction) of the rotary drum 4. In the figure, 2Y indicates the circumferential direction of the rotary drum 4, and X indicates the width direction of the rotary drum 4 (i.e., direction parallel to the rotation axis of the rotary drum 4). As described above, in the present embodiment, the accumulating depression 41 in this manufacturing device 1 is arranged continuously over the entire circumference in the circumferential direction 2Y of the rotary drum 4; instead, the accumulating depression may be configured so that a plurality of accumulating depressions are arranged at predetermined intervals in the circumferential direction 2Y of the rotary drum 4.

As illustrated in FIGS. 3 and 4, the drum body 42 of the rotary drum 4 has therein a plurality of spaces which are independent from one another, and for example, there are three spaces A to C. The spaces A to C are partitioned off from one another by plates provided from the rotation axis side of the rotary drum 4 toward the outer circumferential surface 4*f* side. The rotary drum 4 is connected to an air suction fan (not illustrated) serving as an air suction mechanism. By driving the air suction fan, the pressure in the respective spaces partitioned off inside the rotary drum 4 can be adjusted. In the manufacturing device 1, the suction force in the region corresponding to the space A, which is the upstream region located in a region where the outer circumferential surface 4*f* is covered by the duct 3, can be made stronger or weaker than the suction force in the regions corresponding to the spaces B and C, which are downstream regions, and the space A is maintained at a negative pressure. Note, however, that the manner in which the spaces inside the drum body 42 are partitioned is not limited to the aforementioned configuration. For example, the drum body 42's space A which is maintained at a negative pressure may further be partitioned off into a plurality of spaces, and the pressure in each of the further-partitioned spaces may be adjusted. Further, for example, the drum body 42's space B may further be partitioned off into a plurality of spaces, and the pressure in each of the further-partitioned spaces may be adjusted; further, the pressure in the space located closest to the space A may be adjusted to match the pressure of the space A, so that a negative pressure region can be formed up to a point slightly ahead of where the accumulating depression 41 exits the duct 3.

As illustrated in FIGS. 3 and 4, the member 40 forming the outer circumferential surface 4*f* is arranged so as to cover the entire outer circumference of the drum body 42, and rotates in the direction of arrow R1 about a horizontal axis of the drum body 42 by receiving motive power from a prime mover such as a motor. The accumulating depression 41 is formed in the member 40 forming the outer circumferential surface 4*f*.

The bottom surface of the accumulating depression 41 is constituted by a porous member (not illustrated), and, while the accumulating depression 41 in the outer circumferential surface 4*f* passes over the space in the rotary drum 4 that is maintained at a negative pressure, the porous member functions as suction holes for sucking the materials of the absorbent member 100.

As illustrated in FIGS. 3 and 4, the manufacturing device 1 includes a supplying portion 5 that supplies the sheet fragments 10*bh* to inside the duct 3. The supplying portion 5 includes cutter blades 51, 52 that cut a continuous synthetic fiber sheet 10*bs*, which includes the synthetic fibers 10*b*, at predetermined lengths in the first direction and the second direction, and form the sheet fragments 10*bh*. The supplying portion 5 includes a suction nozzle 58 that sucks the sheet fragments 10*bh* formed by using the cutter blades 51, 52. The supplying portion 5 includes a first cutter roller 53 including a plurality of cutter blades 51 that cut in the first direction, and a second cutter roller 54 including a plurality of cutter blades 52 that cut in the second direction. The supplying portion 5 includes a single receiving roller 55 arranged in opposition to the first cutter roller 53 and the second cutter roller 54.

Figure 5:
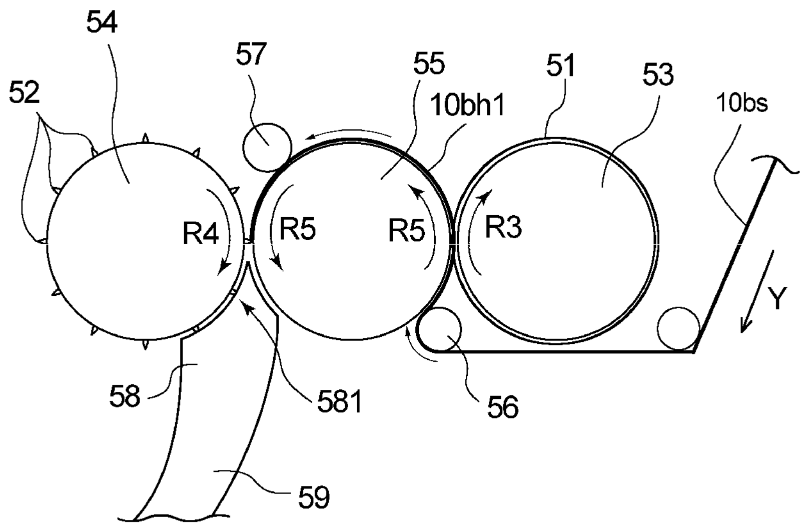
FIG. 5 is an enlarged side view illustrating a supplying portion of the manufacturing device illustrated in FIG. 3.

As illustrated in FIGS. 3 to 5, in the manufacturing device 1, the surface of the first cutter roller 53 is provided with a plurality of cutter blades 51, 51, 51, . . . extending continuously over the entire outer circumference of the first cutter roller 53 along the circumferential direction of the first cutter roller 53, the cutter blades being lined up in the axial direction (X direction) of the first cutter roller 53. In the manufacturing device 1, by receiving motive power from a prime mover such as a motor, the first cutter roller 53 rotates in the direction of arrow R3. The interval between the cutter blades 51, 51, 51, . . . adjacent to one another in the axial direction of the first cutter roller 53 substantially corresponds to the width (length in the lateral direction; length in the X direction) of each sheet fragment 10*bh* formed by cutting and including the synthetic fibers 10*b*. Strictly speaking, depending on the tension during sheet transportation, the synthetic fiber sheet 10*bs* may be cut in a state where it is shrunken in the width direction X; thus, by releasing this tension, the width of each produced sheet fragment 10*bh* may become wider than the interval between the cutter blades 51, 51, 51, . . . .

In the manufacturing device 1, as illustrated in FIGS. 3 to 5, the surface of the second cutter roller 54 is provided with a plurality of cutter blades 52, 52, 52, . . . extending continuously over the entire width of the second cutter roller 54 along the axial direction of the second cutter roller 54, the cutter blades being arranged with intervals therebetween in the circumferential direction of the second cutter roller 54. In the manufacturing device 1, by receiving motive power from a prime mover such as a motor, the second cutter roller 54 rotates in the direction of arrow R4.

As illustrated in FIGS. 3 to 5, in the manufacturing device 1, the receiving roller 55 is a flat roller having a flat surface. By receiving motive power from a prime mover such as a motor, the receiving roller 55 rotates in the direction of arrow R5.

As illustrated in FIGS. 3 and 4, in the manufacturing device 1, opposing the surface of the receiving roller 55, the supplying portion 5 includes, in order from the upstream side toward the downstream side in the rotating direction (the direction of arrow R5): a free roller 56 that introduces the continuous synthetic fiber sheet 10*bs* between the receiving roller 55 and the first cutter roller 53; the first cutter roller 53 that cuts the continuous synthetic fiber sheet 10*bs* in the first direction (Y direction); a nip roller 57 that introduces, between the receiving roller 55 and the second cutter roller 54, a plurality of continuous sheet fragments 10*bh*1 that have been cut in the first direction and extend in the first direction (referred to hereinafter also as "continuous sheet fragment strips 10*bh*1"); and the second cutter roller 54 that cuts the continuous sheet fragment strips 10*bh*1 in the second direction (X direction). The supplying portion 5 also includes a feed roller (not illustrated) that transports the continuous synthetic fiber sheet 10*bs*. The feed roller is configured so as to be rotated by a driving device such as a servomotor. From the viewpoint of preventing the synthetic fiber sheet 10*bs* from slipping, the feed roller may be made less slippery by forming, in the surface thereof, grooves extending in the axial direction over the entire circumference, or by subjecting the entire circumference to a coating treatment for increasing friction force. Further, slipping can be suppressed by sandwiching the sheet between the feed roller and a nip roller.

Figure 6:
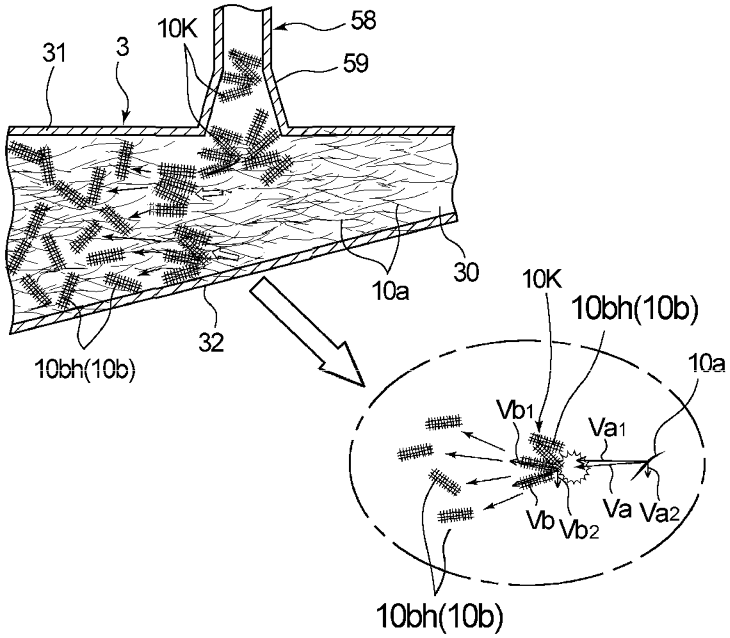
FIG. 6 is a schematic diagram illustrating a state where hydrophilic fibers contact a cluster of sheet fragments inside a duct and the sheet fragments are transported in a dispersed manner.

As illustrated in FIGS. 3 to 5, the supplying portion 5 includes a suction nozzle 58 that sucks the sheet fragments 10*bh* formed by the second cutter roller 54. The suction nozzle 58 has a suction opening 581 that is arranged below the second cutter roller 54—i.e., more toward the downstream side, in the second cutter roller 54's rotating direction (the direction of arrow R4), than the closest point between the second cutter roller 54 and the receiving roller 55. The suction opening 581 of the suction nozzle 58 extends over the entire width of the second cutter roller 54. From the viewpoint of improving the ability to suck the sheet fragments 10*bh*, it is preferable that the suction opening 581 of the suction nozzle 58 is arranged below the receiving roller 55 and the second cutter roller 54 so as to be in opposition between the receiving roller 55 and the second cutter roller 54. From the viewpoint of further improving the ability to suck the sheet fragments 10*bh*, it is preferable that the suction opening 581 of the suction nozzle 58 covers the outer surface of the second cutter roller 54 such that, as viewed from the side surface of the receiving roller 55 and the second cutter roller 54, the length of an arc of the suction opening 581 opposing the second cutter roller 54 is longer than the length of an arc of the suction opening 581 opposing the receiving roller 55, as illustrated in FIG. 6.

As illustrated in FIGS. 3 and 4, the suction nozzle 58 is connected by a supply tube 59 to the top plate 31 side of the duct 3. The sheet fragments 10*bh* sucked from the suction opening 581 of the suction nozzle 58 are supplied to inside the duct 3 in midstream of the duct 3 through the supply tube 59. In the manufacturing device 1, the connecting position of the supply tube 59 and the duct 3 is located between the defibrating portion 2 side and the rotary drum 4 side in the duct 3, and is located more toward the downstream side, in the duct 3, than the absorbent particle dispersing tube 36. The connecting position of the supply tube 59 and the duct 3 is, however, not limited thereto, and for example, it may be on the bottom plate 32 side and not the top plate 31 side of the duct 3.

As illustrated in FIGS. 3 and 4, in the manufacturing device 1, the press-down belt 7 is arranged adjacent to the position of the duct 3 on the downstream side thereof along the rotary drum 4's outer circumferential surface 4*f* located at the space B. In the space B, the pressure is set to zero (atmospheric pressure) or to a negative pressure weaker than that of the space A of the rotary drum 4. The press-down belt 7 is an endless, air-permeable or air-impermeable belt, bridges rollers 71 and 72, and rotates so as to follow the rotation of the rotary drum 4. In cases where the press-down belt 7 is an air-permeable belt, it is preferable that the belt substantially does not allow the material inside the accumulating depression 41 to pass therethrough. Thanks to the press-down belt 7, the accumulation 100*a* in the accumulating depression 41 can be retained inside the accumulating depression 41 until the accumulation is transferred onto the vacuum conveyor 8, even when the pressure in the space B is set to atmospheric pressure.

As illustrated in FIGS. 3 and 4, in the manufacturing device 1, the vacuum conveyor 8 is arranged below the rotary drum 4, and is arranged at the outer circumferential surface 4*f* located in the rotary drum 4's space C in which the pressure is set to zero (atmospheric pressure) or to a slightly positive pressure. A weak positive pressure can be achieved by, for example, blowing air from the inside of the drum body 42 toward outside the outer circumferential surface 4*f* The vacuum conveyor 8 includes: an endless air-permeable belt 83 that bridges a drive roller 81 and driven rollers 82, 82; and a vacuum box 84 arranged in a position opposing the outer circumferential surface 4*f* located at the space C of the rotary drum 4 across the air-permeable belt 83. A core-wrap sheet 100*b*, which is made of tissue paper or a liquid-permeable nonwoven fabric, is introduced onto the vacuum conveyor 8.

Further, in addition to the defibrating portion 2, the duct 3, the rotary drum 4, the supplying portion 5, the press-down belt 7, and the vacuum conveyor 8 described above, the manufacturing device 1 includes folding guide plates (not illustrated), a pressure application portion 9, and a cutting device 6.

In the manufacturing device 1, the folding guide plates (not illustrated) are arranged downstream of the vacuum conveyor 8. The folding guide plates fold, onto the accumulation 100*a*, both lateral sides of the core-wrap sheet 100*b* which extend along the transporting direction (Y direction) so as to cover the accumulation 100*a* transferred onto the core-wrap sheet 100*b* which has been introduced onto the vacuum conveyor 8.

In the manufacturing device 1, the pressure application portion 9 is arranged downstream of the folding guide plates. In the manufacturing device 1, the pressure application portion 9 forms a plurality of depressions 100*e* in the accumulation 100*a* covered by the core-wrap sheet 100*b*. For the pressure application portion 9, it is possible to use, without particular limitation, any means conventionally used for forming depressions in manufacturing absorbent articles, such as sanitary napkins, light incontinence pads, pantiliners, and diapers. In the manufacturing device 1, the pressure application portion 9 includes: an embossing roller 92 on which a plurality of projections 91 are formed on the circumferential surface thereof; and a receiving roller 93 arranged in opposition to the embossing roller 92. In the manufacturing device 1, by receiving motive power from a prime mover such as a motor, the embossing roller 92 rotates in the direction of arrow R6. The shape and pattern of the projections 91 of the embossing roller 92 can be selected appropriately depending on the use. For example, in cases of manufacturing the absorbent member 100 in which the depressions 100*e* are formed according to the pattern illustrated in FIG. 1, a plurality of projections 91 having a corresponding arrangement/pattern may be formed on the circumferential surface of the embossing roller 92. In the manufacturing device 1, the receiving roller 93 is a flat roller having a flat and smooth circumferential surface, and can be made by using a metal or rubber roller, for example. By receiving motive power from a prime mover such as a motor, the receiving roller 93 rotates in the direction of arrow R7. In the manufacturing device 1, the embossing roller 92 and the receiving roller 93 have a heatable structure, and their heating temperatures are controlled by a heating device (not illustrated) so that the synthetic fibers 10*b* of the absorbent member 100 are thermally fusion-bonded. In the manufacturing device 1, at the time of forming the depressions 100*e* by applying pressure to the accumulation 100*a* covered by the core-wrap sheet 100*b*, it is preferable that the embossing roller 92 and/or the receiving roller 93 are/is heated to a predetermined temperature by the heating device.

In the manufacturing device 1, the cutting device 6 is arranged downstream of the pressure application portion 9. In the manufacturing device 1, the cutting device 6 manufactures individual absorbent members 100. For the cutting device 6, it is possible to use, without particular limitation, any type of device conventionally used for cutting a continuous strip of absorbent members in manufacturing absorbent articles, such as sanitary napkins, light incontinence pads, pantiliners, and diapers. In the manufacturing device 1, the cutting device 6 includes a cutter roller 62 having a cutting blade 61 on its circumferential surface, and an anvil roller 63 having a flat and smooth circumferential surface for receiving the cutting blade 61.

Next, a method for manufacturing an absorbent member 100 by using the aforementioned manufacturing device 1—i.e., an embodiment of the absorbent member manufacturing method of the present invention—will be described.

As illustrated in FIGS. 3 and 4, the method for manufacturing the absorbent member 100 according to the present embodiment involves: a transporting step of transporting the hydrophilic fibers 10*a* and a plurality of sheet fragments 10*bh* including the synthetic fibers 10*b* to the accumulating depression 41, serving as an accumulating portion, by using the duct 3, serving as a transporting portion; an accumulating step of accumulating, in the accumulating depression 41 serving as the accumulating portion, the plurality of sheet fragments 10*bh* and the hydrophilic fibers 10*a* transported in the transporting step, and obtaining an accumulation 100*a* which is a constituent member of the absorbent member 100; and a depression forming step of forming depressions 100*e* in the accumulation 100*a* obtained in the accumulating step by applying pressure to portions of the accumulation 100*a*. Further, the method for manufacturing the absorbent member 100 according to the present embodiment involves: a defibrating step of defibrating a continuous hydrophilic sheet 10*as* by using the defibrating machine 21 and obtaining hydrophilic fibers 10*a*; a cutting step of cutting a continuous synthetic fiber sheet 10*bs*, which includes the synthetic fibers 10*b*, at predetermined lengths in the first direction and the second direction, to thereby form sheet fragments 10*bh* including the synthetic fibers 10*b*; and a suction step of sucking the sheet fragments 10*bh* obtained in the cutting step and supplying the sheet fragments to inside the duct 3. Further, the method for manufacturing the absorbent member 100 according to the present embodiment involves a covering step of covering the accumulation 100*a* obtained in the accumulating step with a cover sheet. The method for manufacturing the absorbent member 100 according to the present embodiment will be described in detail below.

First, the space A inside the rotary drum 4 and the inside of the vacuum box 84 for the vacuum conveyor 8 are set to a negative pressure by activating air suction fans (not illustrated) respectively connected thereto. By creating a negative pressure inside the space A, an airflow for transporting the materials of the absorbent member 100 to the outer circumferential surface 4*f* of the rotary drum 4 is created inside the duct 3. Further, the defibrating machine 21 and the rotary drum 4 are rotated, the first cutter roller 53, the second cutter roller 54 and the receiving roller 55 are rotated, and the press-down belt 7 and the vacuum conveyor 8 are activated.

Next, the defibrating step of defibrating a continuous hydrophilic sheet 10*as* by supplying the hydrophilic sheet to the defibrating machine 21 by using the feed rollers 23 and obtaining hydrophilic fibers 10*a* is performed. The pair of feed rollers 23, 23 controls the speed for supplying the hydrophilic sheet 10*as* to the defibrating machine 21. In the defibrating step, the supplying of the hydrophilic sheet 10*as* to the defibrating machine 21 is controlled.

In the defibrating step of the present embodiment, as illustrated in FIGS. 3 and 4, the hydrophilic sheet 10*as* supplied to the defibrating machine 21 is defibrated, and hydrophilic fibers 10*a*, which are a defibrated fiber material, are supplied from the defibrating machine 21 to the duct 3.

The method for manufacturing an absorbent member 100 includes a cutting step separate from the defibrating step. In the cutting step of the present embodiment, as illustrated in FIG. 5, the continuous synthetic fiber sheet 10*bs* is cut at predetermined lengths in the first direction and the second direction and the sheet fragments 10*bh* are formed by using the first cutter roller 53 and the second cutter roller 54. In the cutting step of the present embodiment, by using the first cutter roller 53 which cuts the continuous synthetic fiber sheet 10*bs* at a predetermined length in the first direction (Y direction), the second cutter roller 54 which cuts the sheet at a predetermined length in the second direction (X direction), and a single receiving roller 55 arranged in opposition to the first cutter roller 53 and the second cutter roller 54: the continuous synthetic fiber sheet 10*bs* is introduced between the first cutter roller 53 and the receiving roller 55 and is cut in the first direction to form continuous sheet fragment strips 10*bh*1; and the formed continuous sheet fragment strips 10*bh*1 are transported by the receiving roller 55 and are cut in the second direction between the second cutter roller 54 and the receiving roller 55 to form the sheet fragments 10*bh*. The sheet fragments 10*bh* formed as described above are cut only in the first direction and the second direction. The cutting step of the present embodiment is described in detail below.

In the cutting step of the present embodiment, the synthetic fiber sheet 10*bs* is transported by using the aforementioned feed roller (not illustrated). The feed roller controls the speed for transporting the synthetic fiber sheet 10*bs*. In the cutting step, the transportation speed of the synthetic fiber sheet 10*bs* is controlled.

As illustrated in FIG. 5, in the cutting step of the present embodiment, the synthetic fiber sheet 10*bs* transported by the feed roller is introduced, by the free roller 56, between the receiving roller 55, which is a flat roller rotating in the direction of arrow R5, and the first cutter roller 53, which rotates in the direction of arrow R3, and, with the plurality of cutter blades 51, 51, 51, . . . , the synthetic fiber sheet 10*bs* is cut in the first direction at positions with intervals therebetween in the second direction. Performing cutting as described above forms a plurality of continuous sheet fragment strips 10*bh*1 which extend in the first direction and are arranged side by side in the second direction (X direction). In the present embodiment, the plurality of cutter blades 51, 51, 51, . . . are arranged on the surface of the first cutter roller 53 at even intervals in the second direction. Thus, the synthetic fiber sheet 10*bs* is cut at even intervals, and a plurality of continuous sheet fragment strips 10*bh*1 having the same width (length in the second direction) are formed. From the viewpoint of ensuring that the sheet fragments have the necessary dimensions to achieve predetermined effects, it is preferable that the average width of the sheet fragment strips 10*bh*1 formed in the cutting step is from 0.1 to 10 mm, more preferably from 0.3 to 6 mm, even more preferably from 0.5 to 5 mm. In the present embodiment, the width of each sheet fragment strip 10*bh*1 cut by the first cutter roller 53 matches the length of the side, in the lateral direction, of each sheet fragment 10*bh* ultimately formed. Cutting, however, may be performed such that the width of each sheet fragment strip 10*bh*1 cut by the first cutter roller 53 corresponds to the length of the side, in the length direction, of each sheet fragment 10*bh* ultimately formed. In this case, the average width of the sheet fragment strips 10*bh*1 cut by the first cutter roller 53 is preferably from 0.3 to 30 mm, more preferably from 1 to 15 mm, even more preferably from 2 to 10 mm. The plurality of continuous sheet fragment strips 10*bh*1 that have been formed are transported on the circumferential surface of the receiving roller 55 which rotates in the direction of arrow R5, are transported between the receiving roller 55 and the nip roller 57, and are introduced between the receiving roller 55 and the second cutter roller 54 by the nip roller 57.

Then, as illustrated in FIG. 5, in the cutting step of the present embodiment, the plurality of continuous sheet fragment strips 10*bh*1, which are arranged side by side in the second direction and extend in the first direction, are introduced between the receiving roller 55, which rotates in the direction of arrow R5, and the second cutter roller 54, which rotates in the direction of arrow R4, and, with the plurality of cutter blades 52, 52, 52, . . . , the plurality of continuous sheet fragment strips 10*bh*1 are cut along the second direction and intermittently in the first direction. Performing cutting as described above forms a plurality of rectangular sheet fragments 10*bh* in which the length in the first direction is longer than the length in the second direction. In the present embodiment, the plurality of cutter blades 52, 52, 52, . . . are arranged on the surface of the second cutter roller 54 at even intervals in the circumferential direction thereof. Thus, the plurality of sheet fragment strips 10*bh*1 are cut at even intervals, and a plurality of rectangular sheet fragments 10*bh* having the same length in the first direction are formed. From the viewpoint of ensuring that the sheet fragments have the necessary dimensions to achieve predetermined effects, it is preferable that the average length of each sheet fragment formed in the cutting step is from 0.3 to 30 mm, more preferably from 1 to 15 mm, even more preferably from 2 to 10 mm. In the present embodiment, the length of each sheet fragment 10*bh* cut by the second cutter roller 54 matches the length of the side, in the length direction, of each sheet fragment 10*bh*. Cutting, however, may be performed such that the length of each sheet fragment 10*bh* cut by the second cutter roller 54 corresponds to the length of the side, in the lateral direction, of each sheet fragment 10*bh*. In this case, the length (width) of each sheet fragment 10*bh* cut by the second cutter roller 54 is preferably from 0.1 to 10 mm, more preferably from 0.3 to 6 mm, even more preferably from 0.5 to 5 mm.

In the cutting step of the present embodiment, the continuous synthetic fiber sheet 10*bs* is cut at predetermined lengths in the first direction and the second direction to thereby obtain the sheet fragments 10*bh* including the synthetic fibers 10*b*. Thus, the size of the obtained sheet fragments 10*bh* can easily be adjusted to an intended size. As described above, since sheet fragments with an intended size can be formed with high precision, it is possible to efficiently and continuously manufacture absorbent members having an intended absorbency. It should be noted that, even in cases where the sheet fragments 10*bh* are formed by cutting in the first direction or the second direction by using the first cutter roller 53 including the cutter blades 51 or the second cutter roller 54 including the cutter blades 52, the cutting may make the synthetic fibers fuzzy at the periphery of the formed sheet fragments 10*bh*. Further, if the cutter blades 51, 52 become worn out or otherwise deteriorated due to long-term use, the synthetic fiber sheet 10*bs* may not be cut successfully, which may cause a plurality of the sheet fragments 10*bh* to be connected.

Next, a suction step is performed for sucking the sheet fragments 10*bh*, which have been obtained by cutting with the cutter roller 53, 54, by using the suction nozzle 58 arranged below the second cutter roller 54, and supplying the sheet fragments to inside the duct 3. By arranging the suction opening 581 of the suction nozzle 58 below the second cutter roller 54—i.e., more toward the downstream side, in the second cutter roller 54's rotating direction (the direction of arrow R4 illustrated in FIG. 5), than the closest point between the second cutter roller 54 and the receiving roller 55—the plurality of sheet fragments 10*bh* cut and formed by the second cutter roller 54 and the receiving roller 55 can be sucked efficiently.

Next, a transporting step is performed for transporting the sheet fragments 10*bh* and the hydrophilic fibers 10*a*, which have been supplied to inside the duct 3, to the accumulating depression 41, which serves as the accumulating portion, by using the duct 3. If, as described above, the sheet fragments 10*bh* have a fuzzy periphery or a plurality of sheet fragments 10*bh* are connected, when the sheet fragments 10*bh* are supplied to inside the duct 3, the fuzzy sheet fragments 10*bh* may be joined together and clusters 10K of sheet fragments 10*bh* may be formed, as illustrated in FIG. 6. If clusters 10K of sheet fragments 10*bh* are included in the accumulation 100*a*, the formability of depressions in the later-described depression forming step may deteriorate. So, in the transporting step, the sheet fragments 10*bh* and the hydrophilic fibers 10*a* are brought into contact with one another in the airflow created inside the duct 3, and the sheet fragments 10*bh* and the hydrophilic fibers 10*a* are transported by the airflow in a dispersed and airborne state in which the sheet fragments and the hydrophilic fibers are mixed. In the transporting step of the present embodiment, the sheet fragments 10*bh* and the hydrophilic fibers 10*a* are transported by being supplied at mutually different positions along the flow direction of the airflow in the duct 3. More specifically, in the transporting step, the hydrophilic fibers 10*a* are supplied to inside the flow path 30 of the duct 3 from an upstream side of the duct 3, and the hydrophilic fibers 10*a* are transported, by the airflow flowing inside the flow path 30, toward the rotary drum 4's outer circumferential surface 4*f* from a point more upstream, in the flow direction of the airflow, than the position where the sheet fragments 10*bh* are supplied.

As illustrated in FIGS. 3 and 4, the plurality of sheet fragments 10*bh* sucked in the suction step are supplied through the supply tube 59 of the suction nozzle 58 to inside the flow path 30 of the duct 3 from the top plate 31 side of the duct 3 at a position in midstream of the flow direction of the airflow in the duct 3. An airflow for transporting the hydrophilic fibers 10*a*, which is a material of the absorbent member 100, toward the rotary drum 4's outer circumferential surface 4*f* is created in advance inside the duct 3's flow path 30. Therefore, in the transporting step, when the sheet fragments 10*bh* and the hydrophilic fibers 10*a* merge with one another inside the duct 3, the transportation velocity Vb of the sheet fragments 10*bh* is different from the transportation velocity Va of the hydrophilic fibers 10*a*, and thus, even if clusters 10K of sheet fragments 10*bh* are inadvertently supplied, the clusters 10K of sheet fragments 10*bh* are likely to contact the already-flowing hydrophilic fibers 10*a* and are easily separated into individual sheet fragments 10*bh*. In the transporting step, the velocity component Va1, toward the downstream side, of the transportation velocity Va of the hydrophilic fibers 10*a* is greater than the velocity component Vb1, toward the downstream side, of the transportation velocity Vb of the sheet fragments 10*bh*. Note that the velocity component Va1, toward the downstream side, of the transportation velocity Va of the hydrophilic fibers 10*a* is the velocity component in the horizontal direction when the transportation velocity Va is divided into the horizontal-direction velocity component Va1 and the vertical-direction velocity component Va2 in a projected view when viewing the duct 3 from its side surface, as illustrated in FIG. 6. Similarly, the velocity component Vb1, toward the downstream side, of the transportation velocity Vb of the sheet fragments 10*bh* is the velocity component in the horizontal direction when the transportation velocity Vb is divided into the horizontal-direction velocity component Vb1 and the vertical-direction velocity component Vb2 in a projected view when viewing the duct 3 from its side surface, as illustrated in FIG. 6. As described above, in the transporting step, the hydrophilic fibers 10*a* are supplied from a point more upstream than the sheet fragments 10*bh*. Thus, when the sheet fragments 10*bh* and the hydrophilic fibers 10*a* merge with one another, the velocity component Va1, toward the downstream side, of the hydrophilic fibers 10*a* is greater than the velocity component Vb1, toward the downstream side, of the sheet fragments 10*bh*. Particularly, in the present embodiment, the sheet fragments 10*bh* are supplied to the duct 3's flow path 30 by the supply tube 59 which extends in a direction intersecting with the flow direction of the airflow in the duct 3. Thus, as regards the movement velocity of the sheet fragments 10*bh* immediately before being supplied to the duct 3's flow path 30, the velocity component toward the downstream side in the flow direction in the duct 3 does not become large. Therefore, the velocity component Va1, toward the downstream side, of the transportation velocity Va of the hydrophilic fibers 10*a* is likely to become greater than the velocity component Vb1, toward the downstream side, of the transportation velocity Vb of the sheet fragments 10*bh*. Thus, even if a cluster 10K of sheet fragments 10*bh* is inadvertently supplied into the duct 3's flow path 30, the inadvertently-supplied cluster 10K of sheet fragments 10*bh* contacts the already-flowing hydrophilic fibers 10*a*. As illustrated in FIG. 6, due to the impact of contact with the hydrophilic fibers 10*a*, in the cluster 10K of sheet fragments 10*bh* that has contacted the hydrophilic fibers 10*a*, sections where the sheet fragments 10*bh* have joined together due to cutting failure or excessive tangling caused by the fuzz formed upon cutting are disentangled, and the cluster is separated into individual sheet fragments 10*bh* and transported in a dispersed and airborne state toward the downstream side. In the transporting step, the sheet fragments 10*bh* are separated individually, and the hydrophilic fibers 10*a* and the sheet fragments 10*bh* are transported by the airflow while being mixed in a dispersed and airborne state, and thus, an accumulation 100*a* of an absorbent member 100 in which the sheet fragments 10*bh* and the hydrophilic fibers 10*a* are distributed uniformly can easily be manufactured stably.

Further, in this method for manufacturing an absorbent member 100, in addition to the hydrophilic fibers 10*a*, absorbent particles 10*c* are also supplied to inside the duct 3 to the absorbent member 100. In the transporting step, in addition to the contact between the sheet fragments 10*bh* and the hydrophilic fibers 10*a*, the sheet fragments 10*bh* and the absorbent particles 10*c* are caused to contact one another in the airflow while the sheet fragments 10*bh* and the absorbent particles 10*c* are being transported to the accumulating depression 41, and the sheet fragments 10*bh* are transported in a dispersed and airborne state. The sheet fragments 10*bh*, the absorbent particles 10*c*, and the hydrophilic fibers 10*a* are transported by the airflow in a dispersed and airborne state in which the sheet fragments, the absorbent particles and the hydrophilic fibers are mixed.

In the transporting step, the absorbent particles 10*c* and the sheet fragments 10*bh* are supplied at mutually different positions along the flow direction of the airflow. Further, the absorbent particles 10*c* are supplied and transported at a point more upstream, in the flow direction of the airflow, than the position where the sheet fragments 10*bh* are supplied. Stated differently, as illustrated in FIGS. 3 and 4, the absorbent particle dispersing tube 36 is arranged more toward the upstream side, in the duct 3, than the suction nozzle 58. In the transporting step, the absorbent particles 10*c* are supplied into the duct 3's flow path 30 from a more upstream point of the duct 3 than the suction nozzle 58, and the plurality of sheet fragments 10*bh* having undergone the suction step are supplied into the duct 3's flow path 30 at a more downstream point of the duct 3 than the arrangement position of the absorbent particle dispersing tube 36. In the transporting step, the absorbent particles 10*c* supplied from the absorbent particle dispersing tube 36 into the duct 3's flow path 30 are transported, by the airflow flowing inside the duct 3's flow path 30, toward the rotary drum 4's outer circumferential surface 4*f* from a point more upstream, in the flow direction of the airflow, than the position where the plurality of sheet fragments 10*bh* are supplied.

Figure 7:
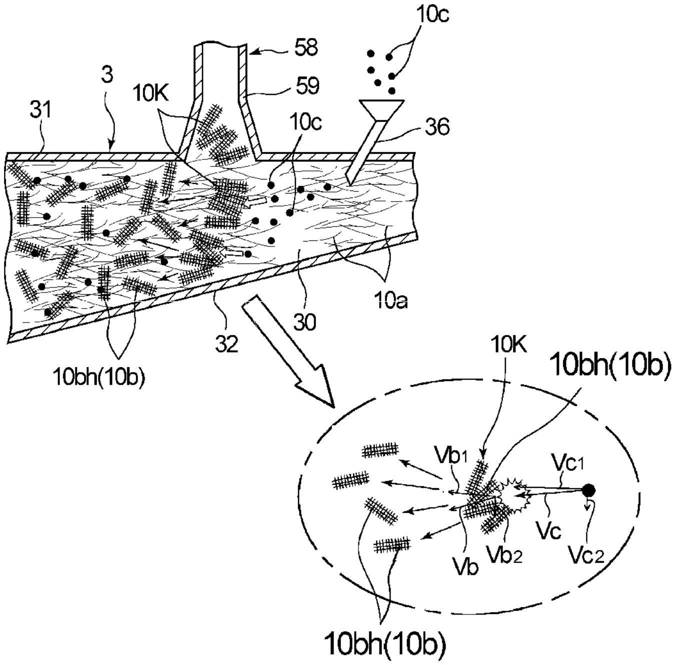
FIG. 7 is a schematic diagram illustrating a state where absorbent particles contact a cluster of sheet fragments inside the duct and the sheet fragments are transported in a dispersed manner.

Herein, in the transporting step of the present embodiment, when the sheet fragments 10*bh* and the absorbent particles 10*c* merge with one another inside the duct 3, the transportation velocity Vb of the sheet fragments 10*bh* is different from the transportation velocity Vc of the absorbent particles 10*c*. Moreover, the velocity component Vc1, toward the downstream side, of the transportation velocity Vc of the absorbent particles 10*c* is greater than the velocity component Vb1, toward the downstream side, of the transportation velocity Vb of the sheet fragments 10*bh*. Note that the velocity component Vc1, toward the downstream side, of the transportation velocity Vc of the absorbent particles 10*c* is the velocity component in the horizontal direction when the transportation velocity Vc is divided into the horizontal-direction velocity component Vc1 and the vertical-direction velocity component Vc2 in a projected view when viewing the duct 3 from its side surface, as illustrated in FIG. 7. In the transporting step, the absorbent particles 10*c* are supplied from a point more upstream than the sheet fragments 10*bh*. Thus, when the sheet fragments 10*bh* and the absorbent particles 10*c* merge with one another, the velocity component Vc1, toward the downstream side, of the absorbent particles 10*c* is greater than the velocity component Vb1, toward the downstream side, of the sheet fragments 10*bh*. Thus, even if a cluster 10K of sheet fragments 10*bh* is inadvertently supplied into the duct 3's flow path 30, the cluster 10K of sheet fragments 10*bh* contacts the already-flowing absorbent particles 10*c*. Then, as regards the cluster 10K of sheet fragments 10*bh* having contacted the absorbent particles 10*c*, the tangling etc. caused by the fuzz formed upon cutting is further disentangled by the impact of contact with the absorbent particles 10*c*, as illustrated in FIG. 7, and the cluster is separated into individual sheet fragments 10*bh* and transported in a dispersed and airborne state toward the downstream side. In the transporting step, since the cluster 10K of sheet fragments 10*bh* contacts the hydrophilic fibers 10*a* in the airflow and also contacts the absorbent particles 10*c* in the airflow, the cluster separates into individual sheet fragments 10*bh* more easily, and the hydrophilic fibers 10*a*, the sheet fragments 10*bh*, and the absorbent particles 10*c* are thus transported by the airflow in a dispersed and airborne state while being mixed. Thus, it is easy to stably manufacture an accumulation 100*a* for an absorbent member 100 in which the hydrophilic fibers 10*a*, the sheet fragments 10*bh*, and the absorbent particles 10*c* are distributed uniformly. Particularly, since the absorbent particles 10*c* have a greater specific gravity than the sheet fragments 10*bh*, the sheet fragments 10*bh* are more easily separated into individual fragments.

Next, an accumulating step is performed for accumulating the sheet fragments 10*bh*, the hydrophilic fibers 10*a*, and also the absorbent particles 10*c* in the accumulating depression 41 arranged in the outer circumferential surface 4*f* of the rotary drum 4 to thereby obtain an accumulation 100*a*. Since the sheet fragments 10*bh* are individually separated in the transporting step and the separated sheet fragments 10*bh* are transported in a dispersed and airborne state, in the accumulating step, the sheet fragments 10*bh* are mixed and accumulated uniformly over substantially the entire region of the accumulation 100*a* in a planar view.

In the aforementioned manner, the sheet fragments 10*bh* are transported such that they are arranged substantially uniformly over the entire region of the accumulating depression 41 of the rotary drum 4, thereby forming an accumulation 100*a*, which is a material of the absorbent member 100, by mixing and accumulating the hydrophilic fibers 10*a*, the sheet fragments 10*bh*, and the absorbent particles 10*c*. Such an accumulation 100*a* formed in the accumulating depression 41 is manufactured continuously over the entire circumference, in the circumferential direction (2Y direction), of the rotary drum 4. After obtaining this accumulation 100*a* in which the hydrophilic fibers 10*a*, the synthetic fibers 10*b*, and the absorbent particles 10*c* have accumulated within the accumulating depression 41, the rotary drum 4 is further rotated, and, while pressing down the accumulation 100*a* in the accumulating depression 41 by the press-down belt 7 which is arranged on the outer circumferential surface 4*f* located at the space B of the rotary drum 4, the accumulation is transported to above the vacuum conveyor 8, as illustrated in FIG. 3.

Then, as illustrated in FIGS. 3 and 4, when the accumulation 100*a* in the accumulating depression 41 reaches a position opposing the vacuum box 84 located at the space C of the rotary drum 4, the accumulation is released from the accumulating depression 41 by suction from the vacuum box 84. Then, the accumulation 100*a*, which extends continuously along the transporting direction Y, is transferred onto the central section, in the width direction X, of the continuous core-wrap sheet 100*b* introduced on the vacuum conveyor 8.

Next, a covering step is performed for covering the accumulation 100*a* with the core-wrap sheet 100*b* serving as a cover sheet. More specifically, as illustrated in FIG. 3, one lateral side of the core-wrap sheet 100*b*, of the two lateral sides which extend along the transporting direction Y, is folded inward in the width direction X onto the accumulation 100*a* by a folding guide plate (not illustrated). Then, the other lateral side is folded inward in the width direction X onto the accumulation 100*a* by a folding guide plate, to thereby manufacture a continuous absorbent member 100 in which the accumulation 100*a* is covered by the core-wrap sheet 100*b*.

Next, a depression forming step is performed for forming depressions 100*e* in the accumulation 100*a* by applying pressure to portions of the accumulation 100*a* obtained in the accumulating step. In the depression forming step, with respect to the continuous absorbent member 100 covered by the core-wrap sheet 100*b*, the depressions 100*e* are formed in the accumulation 100*a* by applying pressure to portions of the accumulation 100*a* from above the core-wrap sheet 100*b*. As illustrated in FIG. 3, in the depression forming step, the continuous absorbent member 100 is introduced between the embossing roller 92, which rotates in the direction of arrow R6 and on which the plurality of projections 91 are formed on the circumferential surface thereof, and a receiving roller 93, which rotates in the direction of arrow R7 and has a flat smooth circumferential surface, and by applying pressure to portions of the absorbent member 100 corresponding to the projections 91 of the embossing roller 92, a plurality of depressions 100*e* are formed in the surface of the absorbent member 100. Since the sheet fragments 10*bh* are present substantially uniformly over the entire region of the accumulation 100*a* in a planar view, it is easy to form the depressions 100*e* in the depression forming step. Stated differently, if clusters 10K of sheet fragments 10*bh* are present in a localized manner in the accumulation 100*a*, then the formability of depressions 100*e* will deteriorate in those portions. In the manufacturing method of the present embodiment, however, it is possible to suppress deterioration in the formability of depressions 100*e*. In the depression forming step, it is preferable that the depressions 100*e* are formed in the surface of the absorbent member 100 by applying pressure while heating. By applying pressure while heating, the synthetic fibers 10*b* in the heated sections are easily fusion-bonded, and the depressions 100*e* can be formed even more easily.

Further, in the aforementioned cutting step, it is preferable to perform cutting such that the average length of the sheet fragments 10*bh*, which are formed by cutting in the first direction and the second direction, is longer than the shortest distance d between adjacent ones of the depressions 100*e* among the plurality of depressions 100*e* formed in the depression forming step. By setting the relationship between the average length of the sheet fragments 10*bh* and the shortest distance d between adjacent depressions 100*e* in this way, a single sheet fragment 10*bh* may be fixed by a plurality of depressions 100*e*, thus making it less likely for the manufactured absorbent member 100 to lose its shape.

Then, the continuous absorbent member 100, which has the depressions 100*e* formed in its surface, is cut at predetermined intervals in the transporting direction Y with the cutting device 6, to thereby manufacture separate absorbent members 100. As illustrated in FIG. 2, each absorbent member 100 manufactured as above includes the accumulation 100*a* made by mixing and accumulating the hydrophilic fibers 10*a*, the sheet fragments 10*bh*, and the absorbent particles 10*c*. The absorbent member 100 is covered by the core-wrap sheet 100*b*, and has the plurality of depressions 100*e* formed from above the core-wrap sheet 100*b*.

As described above, as illustrated in FIG. 3, the method for manufacturing the absorbent member 100 by using the manufacturing device 1 involves: a transporting step of transporting the hydrophilic fibers 10*a* and the plurality of sheet fragments 10*bh* to the accumulating depression 41, serving as an accumulating portion, by using the duct 3, serving as a transporting portion; and an accumulating step of accumulating, in the accumulating depression 41, the plurality of sheet fragments 10*bh* and the hydrophilic fibers 10*a* transported in the transporting step, and obtaining an accumulation 100*a*. Further, the sheet fragments 10*bh* and the hydrophilic fibers 10*a* are brought into contact with one another in an airflow created inside the duct 3, and the sheet fragments 10*bh* and the hydrophilic fibers 10*a* are transported by the airflow in a dispersed and airborne state in which the sheet fragments and the hydrophilic fibers are mixed. Thus, it is easy to form an accumulation 100*a* in which the sheet fragments 10*bh* are dispersed. The manufacturing method of the present embodiment using the manufacturing device 1 further involves a depression forming step of forming depressions 100*e* in the accumulation 100*a* by applying pressure to portions of the accumulation 100*a*. Since the sheet fragments 10*bh* are dispersed in the accumulation 100*a*, it is possible to stably manufacture an absorbent member 100 in which formability of depressions 100*e* by pressure application is improved. By being able to stably form depressions 100*e* in the absorbent member 100, it is possible to control the sparse-dense structure of constituent fibers in the absorbent member 100 and also control the absorbency of the absorbent member 100. Particularly, since pressure is applied to the accumulation 100*a* in a state where the core-wrap sheet 100*b*, serving as a cover sheet, is interposed in between—i.e., in a state where the accumulation is covered by the core-wrap sheet 100*b*—, shape retainability of the absorbent member 100 is improved.

Figure 8:
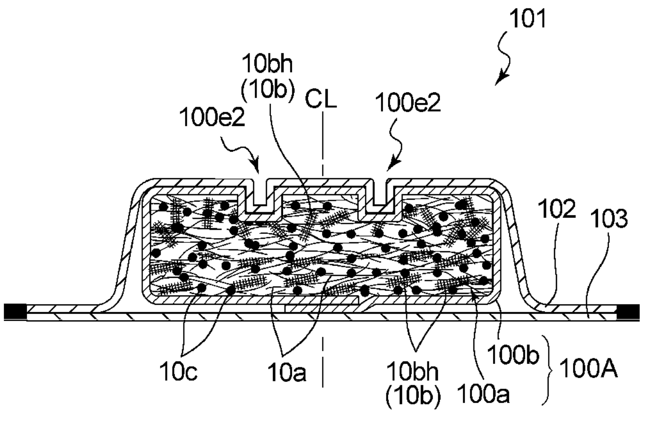
FIG. 8 is a cross-sectional view illustrating a preferred embodiment of an absorbent article manufactured by an absorbent article manufacturing method of the present invention.

Next, a method for manufacturing an absorbent article according to the present invention is described with reference to FIG. 8, taking, as an example, a method for manufacturing a sanitary napkin including the later-described absorbent member 100A (referred to hereinafter simply as "napkin 101"). FIG. 8 illustrates a cross-sectional view of a napkin 101 manufactured according to the absorbent article manufacturing method of the present invention. It should be noted that the description below mainly focuses on features that are different from those in the aforementioned method for manufacturing the absorbent member 100, and explanation on features that are similar to those in the aforementioned method for manufacturing the absorbent member 100 is omitted.

As illustrated in FIG. 8, the napkin 101 includes: a liquid-permeable topsheet 102 forming the skin-facing surface; a backsheet 103 forming the non-skin-facing surface; and an absorbent member 100A interposed between the two sheets 102, 103. The napkin 101 has a shape that is long in the longitudinal direction, which corresponds to the front-rear direction of a wearer when the napkin 101 is worn. The napkin's longitudinal direction matches the longitudinal direction of the absorbent member 100A, and the width direction, which is orthogonal to the longitudinal direction, matches the width direction X of the absorbent member 100A. The planar-view shape of the napkin 101 is not particularly limited, but the napkin is formed so as to be long in the longitudinal direction and have left-right symmetry with respect to a center line CL extending in the longitudinal direction.

As illustrated in FIG. 8, instead of the depressions 100*e* of the aforementioned absorbent member 100, the napkin 101 includes a depression 100*e*2 formed by applying pressure to a portion of the napkin 101 from above the topsheet 102. The depression 100*e*2 is formed so as to be depressed in a recess form from the topsheet 102 side, which faces the wearer's skin when the napkin 101 is worn, toward the backsheet 103 side. In the napkin 101, the depression 100*e*2 is formed such that the skin-facing surface side of the absorbent member 100A of the napkin 101 is depressed in a recess form integrally with the topsheet 102. The depression 100*e*2's shape, in a planar view of the napkin 101 from the topsheet 102 side, is a fully-circumferential groove in which a linearly-formed depressed groove is annularly connected in its entirety. The planar-view shape of the depression 100*e*2 is not particularly limited, and the depression may be formed in a shape/arrangement similar to what is called a leak-prevention groove in this type of absorbent article. Alternatively, the depression is not limited to a linear depressed groove, and a multitude of depressions 100*e*2 having any one of various shapes, such as circular, elliptic, square, rectangular, or triangular, may be arranged intermittently. For the topsheet 102 and the backsheet 103, any one of various materials conventionally used in absorbent articles, such as sanitary napkins, may be used without particular limitation.

Next, a method for manufacturing the napkin 101, which is an embodiment of the absorbent article manufacturing method of the present invention, will be described. The absorbent member 100A used in the napkin 101 is an absorbent member 100A having a structure excluding the depressions 100*e* from the absorbent member 100 manufactured according to the aforementioned method for manufacturing the absorbent member 100. Therefore, in this method for manufacturing the napkin 101, no depression 100*e* is formed in the accumulation 100*a* constituting the absorbent member 100 by applying pressure to the absorbent member 100 in the method for manufacturing the absorbent member 100, but instead, the depression 100*e*2 is formed in the accumulation 100*a* by applying pressure to a portion of the accumulation 100*a* from above the topsheet 102 of the napkin 101. The method for manufacturing the napkin 101 is described below.

In the method for manufacturing the napkin 101, after an absorbent member 100A is manufactured by the manufacturing device 1, a topsheet superposing step is performed for introducing, with an introduction roller, a continuous topsheet 102 supplied from an original textile roll, and superposing the continuous topsheet 102 on the upper surface side of the absorbent member 100A.

Next, the continuous topsheet 102 superposed on the absorbent member 100A is transported between an embossing roller having, on the roller surface, a projection corresponding to the depression 100*e*2 and an anvil roller. Then, a depression forming step is performed by applying pressure, by using the projection, to the topsheet 102 and the absorbent member 100A from above the topsheet 102 toward the lower surface side of the absorbent member 100A, to thereby form the depression 100*e*2 which is integrally depressed. In this way, the depression 100*e*2 is formed in a portion of the accumulation 100*a* of the absorbent member 100A. Like the aforementioned absorbent member 100, the sheet fragments 10*bh* are dispersed in the accumulation 100*a*. Thus, in the napkin 101, formability of the depression 100*e*2 in the accumulation 100*a* is less likely to deteriorate, and it is possible to stably manufacture a napkin 101 in which formability of the depression 100*e*2 is improved.

Next, a backsheet superposing step is performed for introducing, with an introduction roller, a continuous backsheet 103 supplied from an original textile roll, and superposing the continuous backsheet 103 on the lower surface side of the absorbent member 100A which has been integrated with the topsheet 102. Then, the absorbent member 100A sandwiched between the topsheet 102 and the backsheet 103 is sealed in a shape corresponding to the shape of the product, to form a continuous strip of napkins 101. Then, the continuous strip of napkins 101 is cut along the sealed sections, to thereby manufacture individual napkins 101.

In the aforementioned method for manufacturing the napkin 101, the absorbent member 100A including no depression 100*e* is used as the absorbent member. However, it is possible to use an absorbent member 100 including a depression 100*e*. A method for manufacturing a napkin 101 including an absorbent member 100 having a depression 100*e* may involve, for example: a depression forming step for forming a depression 100*e* in the accumulation 100*a* constituting the absorbent member 100 by applying pressure to a portion of the accumulation 100*a*; and also, a depression forming step for forming a depression 100*e*2 in the accumulation 100*a* by applying pressure to a portion of the accumulation 100*a* from above the topsheet 102 of the napkin 101.

The present invention is not limited to the foregoing embodiments and can be modified as appropriate.

For example, in the aforementioned method for manufacturing the absorbent member 100, the absorbent particles 10*c* are supplied by using the absorbent particle dispersing tube 36, but the absorbent particles 10*c* do not have to be supplied. That is, in the transporting step of the present embodiment, the hydrophilic fibers 10*a* and the absorbent particles 10*c* are made to contact clusters 10K of sheet fragments 10*bh* that have inadvertently been supplied in order to separate the clusters into individual sheet fragments 10*bh*, but only the hydrophilic fibers 10*a* may be made to contact the clusters 10K of sheet fragments 10*bh* to separate them.

Further, in the depression forming step of the present embodiment, the depressions 100*e* are formed by applying pressure in a state where the core-wrap sheet 100*b*, serving as a cover sheet covering the accumulation 100*a*, is interposed in between. Instead, depressions 100*e* may be formed by applying pressure directly to an accumulation 100*a* that is not covered by a cover sheet. Alternatively, depressions may be formed, for example, by applying pressure in a state where another sheet arranged on the skin-facing surface side of the absorbent member 100 is interposed in between in addition to the core-wrap sheet 100*b*.

Further, in the transporting step of the present embodiment, the hydrophilic fibers 10*a* are supplied at a position more upstream than the position where the sheet fragments 10*bh* are supplied. Instead, the hydrophilic fibers 10*a* may be supplied at a position more downstream than the position where the sheet fragments 10*bh* are supplied. In cases where the position for supplying the hydrophilic fibers 10*a* is more downstream than the position where the sheet fragments 10*bh* are supplied, even if clusters 10K of sheet fragments 10*bh* are supplied inadvertently, the clusters 10K of sheet fragments 10*bh* flowing in from the upstream side will contact the hydrophilic fibers 10*a* in the airflow when the sheet fragments 10*bh* and the hydrophilic fibers 10*a* merge together, and thus, the clusters 10K will be separated into individual sheet fragments 10*bh* and be transported on the airflow in a dispersed and airborne state. Thus, it is easy to form an accumulation 100*a* in which the sheet fragments 10*bh* including the synthetic fibers 10*b* are dispersed, and it is possible to stably manufacture an absorbent member 100 in which formability of depressions 100*e* by pressure application is improved.

Further, in the transporting step of the present embodiment, the absorbent particles 10*c* are supplied at a position more upstream than the position where the sheet fragments 10*bh* are supplied. Instead, the absorbent particles 10*c* may be supplied at a position more downstream than the position where the sheet fragments 10*bh* are supplied. In cases where the position for supplying the absorbent particles 10*c* is more downstream than the position where the sheet fragments 10*bh* are supplied, even if clusters 10K of sheet fragments 10*bh* are supplied inadvertently, the clusters 10K of sheet fragments 10*bh* flowing in from the upstream side will contact the absorbent particles 10*c* in the airflow when the sheet fragments 10*bh* and the absorbent particles 10*c* merge together, and thus, the clusters 10K will be separated into individual sheet fragments 10*bh* and be transported on the airflow in a dispersed and airborne state. Thus, it is easy to form an accumulation 100*a* in which the sheet fragments 10*bh* including the synthetic fibers 10*b* are dispersed, and it is possible to stably manufacture an absorbent member 100 in which formability of depressions 100*e* by pressure application is improved.

Further, in the method for manufacturing the absorbent member 100, the sheet fragments 10*bh* are formed in the cutting step, but the cutting step does not have to be provided in-line. Instead, it is possible to use sheet fragments 10*bh* having been cut into predetermined lengths in advance. Further, in the cutting step of the present embodiment, the synthetic fiber sheet 10*bs* is cut by using the first cutter roller 53 and the second cutter roller 54, but instead of using two cutter rollers, the synthetic fiber sheet 10*bs* may be cut by using a single cutter roller having, on the same circumferential surface, cutter blades 51 that cut in the first direction and cutter blades 52 that cut in the second direction. In cases of using this single cutter roller, it is preferable to use a single receiving roller arranged in opposition to the single cutter roller. In a manufacturing device including the single cutter roller and the single receiving roller, it is preferable to arrange the suction opening 581 of the suction nozzle 58 below the single cutter roller.

Further, in the cutting step of the present embodiment, the sheet fragments 10*bh* including the synthetic fibers 10*b* are manufactured by cutting the continuous synthetic fiber sheet 10*bs* at predetermined lengths in the first direction and the second direction by using the first cutter roller 53 including the cutter blades 51 that cut in the first direction, the second cutter roller 54 including the cutter blades 52 that cut in the second direction, and a single receiving roller 55 arranged in opposition to the first cutter roller 53 and the second cutter roller 54. Instead, the sheet fragments 10*bh* may be manufactured by cutting the synthetic fiber sheet 10*bs* by using separate receiving rollers respectively arranged in opposition to the first cutter roller 53 and the second cutter roller 54.

Further, in the cutting step of the present embodiment, sheet fragments 10*bh* having the same size are manufactured by cutting the synthetic fiber sheet 10*bs* by using the first cutter roller 53 having a plurality of cutter blades 51 arranged at even intervals and the second cutter roller 54 having a plurality of cutter blades 52 arranged at even intervals, as illustrated in FIG. 3. Instead, the sheet fragments 10*bh* may be manufactured by cutting the synthetic fiber sheet 10*bs* by using a first cutter roller 53 having a plurality of cutter blades 51 arranged at two or more types of intervals, or a second cutter roller 54 having a plurality of cutter blades 52 arranged at two or more types of intervals. Manufacturing in this way can form sheet fragments 10*bh* having two or more sizes, but unlike manufacturing by employing a cutter mill system, sheet fragments with intended sizes can be formed with high precision, and absorbent members having an intended absorbency can be manufactured efficiently and continuously.

Further, as illustrated in FIG. 3, in the cutting step of the present embodiment, the sheet fragments 10*bh* are manufactured by cutting the synthetic fiber sheet 10*bs* by using the first cutter roller 53 and the second cutter roller 54, but instead of using cutter rollers, the sheet fragments 10*bh* may be manufactured by cutting the synthetic fiber sheet 10*bs* by using a press machine including cutter blades 51 that cut in the first direction and a press machine including cutter blades 52 that cut in the second direction.

Further, in the transporting step of the present embodiment, as illustrated in FIG. 3, the absorbent particles 10*c* are supplied to inside the duct 3 by using the absorbent particle dispersing tube 36, but the supplying of the absorbent particles 10*c* is not limited to the absorbent particle dispersing tube 36, and any other means capable of supplying the absorbent particles 10*c* may be used.

The shape of the accumulation 100*a* to be manufactured may be changed flexibly by changing the shape of the accumulating depression 41. Further, the fibers used for the synthetic fibers 10*b* may be subjected to a hydrophilizing treatment.

In relation to the foregoing embodiments, the following absorbent member manufacturing methods are further disclosed.

{1}

A method for manufacturing an absorbent member for an absorbent article, the absorbent member including synthetic fibers and hydrophilic fibers, the method comprising:

a transporting step of transporting the hydrophilic fibers and a plurality of sheet fragments including the synthetic fibers to an accumulating portion by using a transporting portion;

an accumulating step of accumulating, in the accumulating portion, the plurality of sheet fragments and the hydrophilic fibers transported in the transporting step, and obtaining an accumulation which is a constituent member of the absorbent member; and a depression forming step of forming a depression in the accumulation obtained in the accumulating step by applying pressure to a portion of the accumulation, wherein:

in the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed.

{2}

The method for manufacturing an absorbent member as set forth in clause {1}, wherein:

the method further comprises a covering step of covering the accumulation obtained in the accumulating step with a cover sheet; and in the depression forming step, the depression is formed in the accumulation by applying pressure to the accumulation from above the cover sheet.

{3}

The method for manufacturing an absorbent member as set forth in clause {1} or {2}, wherein, in the transporting step, the sheet fragments and the hydrophilic fibers are transported by being supplied at mutually different positions along a flow direction of the airflow in the transporting portion.

{4}

The method for manufacturing an absorbent member as set forth in clause {3}, wherein, in the transporting step, the hydrophilic fibers are transported by being supplied at a point more upstream, in the flow direction, than the position where the sheet fragments are supplied.

{5}

The method for manufacturing an absorbent member as set forth in clause {3} or {4}, wherein, in the transporting step, when the sheet fragments and the hydrophilic fibers merge with one another inside the transporting portion, the transportation velocity of the sheet fragments is different from the transportation velocity of the hydrophilic fibers.

{6}

The method for manufacturing an absorbent member as set forth in any one of clauses {1} to {5}, wherein, in the transporting step:

absorbent particles are further supplied to inside the transporting portion; and the sheet fragments and the absorbent particles are brought into contact with one another in the airflow, and the sheet fragments, the absorbent particles, and the hydrophilic fibers are transported by the airflow in a dispersed and airborne state in which the sheet fragments, the absorbent particles, and the hydrophilic fibers are mixed.

{7}

The method for manufacturing an absorbent member as set forth in clause {6}, wherein, in the transporting step, the sheet fragments and the absorbent particles are transported by being supplied at mutually different positions along the flow direction.

{8}

The method for manufacturing an absorbent member as set forth in clause {7}, wherein, in the transporting step, the absorbent particles are supplied at a position more upstream, in the flow direction, than the position where the sheet fragments are supplied.

{9}

The method for manufacturing an absorbent member as set forth in clause {7} or {8}, wherein, in the transporting step, when the sheet fragments and the absorbent particles merge with one another inside the transporting portion, the transportation velocity of the sheet fragments is different from the transportation velocity of the absorbent particles.

{10}

The method for manufacturing an absorbent member as set forth in any one of clauses {1} to {9}, wherein, in the depression forming step, the depression is formed by applying pressure to the accumulation while heating.

{11}

The method for manufacturing an absorbent member as set forth in any one of clauses {1} to {10}, wherein the method further comprises a cutting step of cutting a continuous synthetic fiber sheet including the synthetic fibers at predetermined lengths in a first direction and a second direction intersecting with the first direction, and forming the sheet fragments.

{12}

The method for manufacturing an absorbent member as set forth in clause {11}, wherein:

in the depression forming step, a plurality of the depressions are formed in the accumulation; and an average length of the sheet fragments formed in the cutting step is longer than a shortest distance between adjacent ones of the depressions among the plurality of depressions formed in the depression forming step.

{13}

The method for manufacturing an absorbent member as set forth in clause {11} or {12}, wherein the average length of the sheet fragments formed in the cutting step is preferably from 0.3 to 30 mm, more preferably from 1 to 15 mm, even more preferably from 2 to 10 mm.

{14}

The method for manufacturing an absorbent member as set forth in any one of clauses {11} to {13}, wherein an average width of the sheet fragments formed in the cutting step is preferably from 0.1 to 10 mm, more preferably from 0.3 to 6 mm, even more preferably from 0.5 to 5 mm.

{15}

A method for manufacturing an absorbent article that includes a liquid-permeable topsheet forming a skin-facing surface, a backsheet forming a non-skin-facing surface, and an absorbent member interposed between the topsheet and the backsheet, the absorbent article manufacturing method comprising:

a transporting step of transporting hydrophilic fibers and a plurality of sheet fragments including synthetic fibers to an accumulating portion by using a transporting portion;

an accumulating step of accumulating, in the accumulating portion, the plurality of sheet fragments and the hydrophilic fibers transported in the transporting step, and obtaining an accumulation which is a constituent member of the absorbent member;

a topsheet superposing step of superposing the topsheet on an upper surface side of the accumulation;

a backsheet superposing step of superposing the backsheet on a lower surface side of the accumulation; and a depression forming step of forming a depression in the accumulation by applying pressure to a portion of the accumulation, wherein:

in the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed.

{16}

The method for manufacturing an absorbent article as set forth in clause {15}, wherein, in the depression forming step, the depression is formed in the accumulation by applying pressure to the accumulation from above the topsheet superposed on the accumulation.

{17}

The method for manufacturing an absorbent article as set forth in clause {15} or {16}, wherein:

the method further comprises a covering step of covering the accumulation obtained in the accumulating step with a cover sheet; and in the topsheet superposing step and the backsheet superposing step, the topsheet and the backsheet are superposed on the absorbent member made by covering the accumulation with the cover sheet.

{18}

The method for manufacturing an absorbent article as set forth in any one of clauses {15} to {17}, wherein, in the transporting step, the sheet fragments and the hydrophilic fibers are transported by being supplied at mutually different positions along a flow direction of the airflow in the transporting portion.

{19}

The method for manufacturing an absorbent article as set forth in clause {18}, wherein, in the transporting step, the hydrophilic fibers are transported by being supplied at a point more upstream, in the flow direction, than the position where the sheet fragments are supplied.

{20}

The method for manufacturing an absorbent article as set forth in clause {18} or {19}, wherein, in the transporting step, when the sheet fragments and the hydrophilic fibers merge with one another inside the transporting portion, the transportation velocity of the sheet fragments is different from the transportation velocity of the hydrophilic fibers.

{21}

The method for manufacturing an absorbent article as set forth in any one of clauses {15} to {20}, wherein, in the transporting step:

absorbent particles are further supplied to inside the transporting portion; and the sheet fragments and the absorbent particles are brought into contact with one another in the airflow, and the sheet fragments, the absorbent particles, and the hydrophilic fibers are transported by the airflow in a dispersed and airborne state in which the sheet fragments, the absorbent particles, and the hydrophilic fibers are mixed.

{22}

The method for manufacturing an absorbent article as set forth in clause {21}, wherein, in the transporting step, the sheet fragments and the absorbent particles are transported by being supplied at mutually different positions along the flow direction.

{23}

The method for manufacturing an absorbent article as set forth in clause {22}, wherein, in the transporting step, the absorbent particles are supplied at a position more upstream, in the flow direction, than the position where the sheet fragments are supplied.

{24}

The method for manufacturing an absorbent article as set forth in any one of clauses {21} to {23}, wherein, in the transporting step, when the sheet fragments and the absorbent particles merge with one another inside the transporting portion, the transportation velocity of the sheet fragments is different from the transportation velocity of the absorbent particles.

{25}

The method for manufacturing an absorbent article as set forth in any one of clauses {15} to {24}, wherein, in the depression forming step, the depression is formed by applying pressure to the accumulation while heating.

{26}

The method for manufacturing an absorbent article as set forth in any one of clauses {15} to {24}, wherein the method further comprises a cutting step of cutting a continuous synthetic fiber sheet including the synthetic fibers at predetermined lengths in a first direction and a second direction intersecting with the first direction, and forming the sheet fragments.

{27}

The method for manufacturing an absorbent article as set forth in clause {26}, wherein:

in the depression forming step, a plurality of the depressions are formed in the accumulation; and an average length of the sheet fragments formed in the cutting step is longer than a shortest distance between adjacent ones of the depressions among the plurality of depressions formed in the depression forming step.

{28}

The method for manufacturing an absorbent article as set forth in clause {26} or {27}, wherein the average length of the sheet fragments formed in the cutting step is preferably from 0.3 to 30 mm, more preferably from 1 to 15 mm, even more preferably from 2 to 10 mm.

{29}

The method for manufacturing an absorbent article as set forth in any one of clauses {26} to {28}, wherein an average width of the sheet fragments formed in the cutting step is preferably from 0.1 to 10 mm, more preferably from 0.3 to 6 mm, even more preferably from 0.5 to 5 mm.

INDUSTRIAL APPLICABILITY

In manufacturing absorbent members that include hydrophilic fibers and sheet fragments including synthetic fibers, the present invention enables stable manufacturing of absorbent members having improved formability of depressions formed by applying pressure.

The invention claimed is:

1. A method for manufacturing an absorbent member for an absorbent article, the absorbent member including synthetic fibers and hydrophilic fibers, the method comprising:

a transporting step of transporting the hydrophilic fibers and a plurality of sheet fragments, which comprise the synthetic fibers, to an accumulating portion by using a transporting portion;

an accumulating step of accumulating, in the accumulating portion, the plurality of sheet fragments and the hydrophilic fibers transported in the transporting step, and obtaining an accumulation which is a constituent member of the absorbent member; and a depression forming step of forming a depression in the accumulation obtained in the accumulating step by applying pressure to a portion of the accumulation, wherein:

in the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed; and wherein the method further comprises a cutting step of cutting a continuous synthetic fiber sheet including the synthetic fibers at predetermined lengths in a first direction and a second direction intersecting with the first direction, and forming the sheet fragments.

2. The method for manufacturing an absorbent member according to claim 1, wherein:

the method further comprises a covering step of covering the accumulation obtained in the accumulating step with a cover sheet; and in the depression forming step, the depression is formed in the accumulation by applying pressure to the accumulation from above the cover sheet.

3. The method for manufacturing an absorbent member according to claim 1, wherein, in the transporting step, the sheet fragments and the hydrophilic fibers are transported by being supplied at mutually different positions along a flow direction of the airflow in the transporting portion.

4. The method for manufacturing an absorbent member according to claim 3, wherein, in the transporting step, the hydrophilic fibers are transported by being supplied at a point more upstream, in the flow direction, than the position where the sheet fragments are supplied.

5. The method for manufacturing an absorbent member according to claim 3, wherein, in the transporting step, when the sheet fragments and the hydrophilic fibers merge with one another inside the transporting portion, the transportation velocity of the sheet fragments is different from the transportation velocity of the hydrophilic fibers.

6. The method for manufacturing an absorbent member according to claim 1, wherein, in the transporting step:

absorbent particles are further supplied to inside the transporting portion; and the sheet fragments and the absorbent particles are brought into contact with one another in the airflow, and the sheet fragments, the absorbent particles, and the hydrophilic fibers are transported by the airflow in a dispersed and airborne state in which the sheet fragments, the absorbent particles, and the hydrophilic fibers are mixed.

7. The method for manufacturing an absorbent member according to claim 6, wherein, in the transporting step, the sheet fragments and the absorbent particles are transported by being supplied at mutually different positions along the flow direction of the airflow in the transporting portion.

8. The method for manufacturing an absorbent member according to claim 7, wherein, in the transporting step, the absorbent particles are supplied at a position more upstream, in the flow direction, than the position where the sheet fragments are supplied.

9. The method for manufacturing an absorbent member according to claim 1, wherein:

in the depression forming step, a plurality of the depressions are formed in the accumulation; and an average length of the sheet fragments formed in the cutting step is longer than a shortest distance between adjacent ones of the depressions among the plurality of depressions formed in the depression forming step.

10. A method for manufacturing an absorbent article that includes a liquid-permeable topsheet forming a skin-facing surface, a backsheet forming a non-skin-facing surface, and an absorbent member interposed between the topsheet and the backsheet, the absorbent article manufacturing method comprising:

a transporting step of transporting hydrophilic fibers and a plurality of sheet fragments, which comprise synthetic fibers to an accumulating portion by using a transporting portion;

an accumulating step of accumulating, in the accumulating portion, the plurality of sheet fragments and the hydrophilic fibers transported in the transporting step, and obtaining an accumulation which is a constituent member of the absorbent member;

a topsheet superposing step of superposing the topsheet on an upper surface side of the accumulation;

a backsheet superposing step of superposing the backsheet on a lower surface side of the accumulation; and a depression forming step of forming a depression in the accumulation by applying pressure to a portion of the accumulation, wherein:

in the transporting step, the sheet fragments and the hydrophilic fibers are brought into contact with one another in an airflow created inside the transporting portion, and the sheet fragments and the hydrophilic fibers are transported by the airflow in a dispersed and airborne state in which the sheet fragments and the hydrophilic fibers are mixed; and wherein the method further comprises a cutting step of cutting a continuous synthetic fiber sheet including the synthetic fibers at predetermined lengths in a first direction and a second direction intersecting with the first direction, and forming the sheet fragments.

11. The method for manufacturing an absorbent article according to claim 10, wherein, in the depression forming step, the depression is formed in the accumulation by applying pressure to the accumulation from above the topsheet superposed on the accumulation.

12. The method for manufacturing an absorbent article according to claim 10, wherein:

the method further comprises a covering step of covering the accumulation obtained in the accumulating step with a cover sheet; and in the topsheet superposing step and the backsheet superposing step, the topsheet and the backsheet are superposed on the absorbent member made by covering the accumulation with the cover sheet.

13. The method for manufacturing an absorbent article according to claim 10, wherein, in the transporting step, the sheet fragments and the hydrophilic fibers are transported by being supplied at mutually different positions along a flow direction of the airflow in the transporting portion.

14. The method for manufacturing an absorbent article according to claim 13, wherein, in the transporting step, the hydrophilic fibers are transported by being supplied at a point more upstream, in the flow direction, than the position where the sheet fragments are supplied.

15. The method for manufacturing an absorbent article according to claim 10, wherein, in the transporting step:

absorbent particles are further supplied to inside the transporting portion; and the sheet fragments and the absorbent particles are brought into contact with one another in the airflow, and the sheet fragments, the absorbent particles, and the hydrophilic fibers are transported by the airflow in a dispersed and airborne state in which the sheet fragments, the absorbent particles, and the hydrophilic fibers are mixed.

16. The method for manufacturing an absorbent article according to claim 15, wherein, in the transporting step, the sheet fragments and the absorbent particles are transported by being supplied at mutually different positions along the flow direction of the airflow in the transporting portion.

17. The method for manufacturing an absorbent article according to claim 16, wherein, in the transporting step, the absorbent particles are supplied at a position more upstream, in the flow direction, than the position where the sheet fragments are supplied.

18. The method for manufacturing an absorbent article according to claim 10, wherein:

in the depression forming step, a plurality of the depressions are formed in the accumulation; and an average length of the sheet fragments formed in the cutting step is longer than a shortest distance between adjacent ones of the depressions among the plurality of depressions formed in the depression forming step.

* * * * *